(12) United States Patent
Mears

(10) Patent No.: US 12,191,024 B2
(45) Date of Patent: Jan. 7, 2025

(54) AUTONOMOUS MANAGEMENT OF A DIABETIC CONDITION BASED ON MEALTIME AND ACTIVITY DETECTION

(71) Applicant: Roche Diabetes Care, Inc., Indianapolis, IN (US)

(72) Inventor: Mark Gilmore Mears, Wesfield, IN (US)

(73) Assignee: Roche Diabetes Care, Inc., Indianapolis, IN (US)

( * ) Notice: Subject to any disclaimer, the term of this patent is extended or adjusted under 35 U.S.C. 154(b) by 406 days.

(21) Appl. No.: 17/316,240

(22) Filed: May 10, 2021

(65) Prior Publication Data

US 2021/0265035 A1    Aug. 26, 2021

Related U.S. Application Data

(63) Continuation of application No. 16/291,584, filed on Mar. 4, 2019, now Pat. No. 11,031,116.

(51) Int. Cl.
*G16H 20/60*      (2018.01)
*G06V 20/20*      (2022.01)
(Continued)

(52) U.S. Cl.
CPC ............. *G16H 20/60* (2018.01); *G06V 20/20* (2022.01); *G16H 20/17* (2018.01); *G16H 40/63* (2018.01); *H04W 4/029* (2018.02)

(58) Field of Classification Search
CPC ........ G16H 20/60; G16H 20/10; G16H 40/60; G16H 50/30; G16H 80/00; G16H 20/00
See application file for complete search history.

(56) References Cited

U.S. PATENT DOCUMENTS 7,879,026 B2    2/2011   Estes et al.
9,847,038 B2   12/2017   Mayou et al.
(Continued)

FOREIGN PATENT DOCUMENTS

WO    WO 2017-136218 A1    8/2017
WO    WO-2019157102 A1 *   8/2019   ........... A61B 5/0022

OTHER PUBLICATIONS

Chen, Sanjian, et al. "Towards a model-based meal detector for type I diabetics." (2015). (Year: 2015).*

(Continued)

*Primary Examiner* — Jason B Dunham
*Assistant Examiner* — Constantine Siozopoulos
(74) *Attorney, Agent, or Firm* — Flaster Greenberg P.C.

(57) ABSTRACT

Management of a diabetic condition may be performed by detecting a mealtime and/or an increased level of activity associated with a user. The mealtime is detected based one or more mealtime indicators that may indicate a likelihood of an occurrence of a mealtime. Each mealtime indicator provides additional context around the likelihood of a mealtime. To assist in managing the diabetic condition, a user's elevated activity levels may be detected. The activity level of a user is detected based on one or more activity indicators. Each activity indicator provides additional context around the likelihood of an increased level of activity by the user. Management of the diabetic condition may be performed proximate a mealtime or a user exercising to increase the efficacy of management of the diabetic condition.

30 Claims, 14 Drawing Sheets

(51) Int. Cl.
    *G16H 20/17*     (2018.01)
    *G16H 40/63*     (2018.01)
    *H04W 4/029*     (2018.01)

(56) References Cited

U.S. PATENT DOCUMENTS

| | | |
|---|---|---|
| 10,792,423 B2 | 10/2020 | Chen et al. |
| 2011/0124996 A1 | 5/2011 | Reinke et al. |
| 2014/0099614 A1 | 4/2014 | Hu et al. |
| 2014/0135592 A1 | 5/2014 | Ohnemus et al. |
| 2014/0275748 A1 | 9/2014 | Dunki-Jacobs et al. |
| 2014/0349256 A1 | 11/2014 | Conner |
| 2015/0118658 A1 | 4/2015 | Mayou et al. |
| 2016/0005299 A1 | 1/2016 | Zomet et al. |
| 2016/0063692 A1 | 3/2016 | Divakaran et al. |
| 2016/0287142 A1 | 4/2016 | Han et al. |
| 2016/0350514 A1 | 12/2016 | Rajendran et al. |
| 2017/0249445 A1 | 8/2017 | Devries et al. |
| 2018/0137937 A1 | 5/2018 | Gass et al. |
| 2020/0135320 A1* | 4/2020 | Vleugels ................ G16H 20/13 |

OTHER PUBLICATIONS

CIPA: DC-008-2016, "Exchangeable image file format for digital still cameras: Exif Version 2.31", Standard of the Camera & Imaging Products Association, Jul. 2016, 191 pages.

\* cited by examiner

AUTONOMOUS MANAGEMENT OF A DIABETIC CONDITION BASED ON MEALTIME AND ACTIVITY DETECTION

CROSS-REFERENCE TO RELATED APPLICATION

This application is a continuation of U.S. patent application Ser. No. 16/291,584, filed Mar. 4, 2019, which is incorporated by reference herein in its entirety.

TECHNICAL FIELD

This disclosure relates to systems and methods for the management of diabetes mellitus generally and, more specifically, to systems and methods for the autonomous management of diabetes based on the detection of mealtimes and activity of a person with diabetes.

BACKGROUND

Management of a medical condition, such as diabetes, requires regular treatment by the person with the medical condition. For example, in order to properly treat a diabetic condition, an individual may have to perform a number of action proximate to (e.g., before and/or after) a mealtime or engaging in exercise, as a meal or exercise may cause the blood glucose levels of the individual to fluctuate significantly.

Individuals may not consistently perform proper treatment of the diabetic condition, for example, because the individual forgets to perform one or more forms of treatment in a timely manner. The many forms of treatment make proper treatment difficult to maintain. Individuals with diabetes may need to take medication, measure pre- and/or post-meal blood glucose levels, record an amount of carbs consumed during a meal, record some dimension about a meal consumed, use a bolus insulin calculator to determine an amount of insulin to inject, inject a meal bolus of insulin, and/or record a meal bolus insulin amount, among other forms of treatment. The improper treatment of the diabetic condition causes an individual to enter an extreme diabetic state (e.g., a hyperglycemic or hypoglycemic state).

Some current diabetic treatment systems attempt to inform a user as to when to perform certain times of treatment. Such systems tend to generate too many alerts and provide the alerts well before or after they are helpful to the person with the diabetic condition, as an individual's mealtime and exercise schedule are generally unpredictable. Generating such alerts causes unnecessary processing and may cause a drain on the battery of battery-powered devices.

In addition to providing alerts, some diabetic treatment systems inject insulin to treat an individual's diabetic condition using, for example, automatic insulin pumps. Some people mistakenly believe that an insulin pump automatically delivers exactly the appropriate levels of insulin to the individual's body and is hassle-free. However, using an insulin pump requires more attention than traditional insulin injections. For example, although a continuous infusion of insulin is automatically delivered throughout the day (e.g., basal insulin), bursts of insulin are also manually delivered by an individual (e.g., bolus of insulin).

SUMMARY

Management of a diabetic condition may be autonomously performed based on a user's activity. Management of the diabetic condition includes determining whether a user has consumed a meal (e.g., mealtime detection). Mealtime detection includes the detection of one or more mealtime indicators that indicate a likelihood that a mealtime is occurring, has occurred, or will occur. Each mealtime indicator provides additional context around the likelihood of a mealtime.

A mealtime score is determined based on the detected mealtime indicators. The mealtime indicators are respectively assigned a weight. The detected mealtime indicator weights are summed together to determine a mealtime score. The mealtime score is compared to a threshold number of detected mealtime indicators. For example, the threshold may be detecting at least three mealtime indicators. When the mealtime score is above the threshold, the user may be about to consume a meal and management of the diabetic condition may be performed.

As described herein, mealtime indicators include: a predefined meal-time indicator, a location indicator, a position indicator, a blood glucose indicator, a photo indicator, or a keyword indicator. The predefined meal-time indicator is detected at estimated mealtimes associated with the user (e.g., 7 am, 12 pm, and/or 6 pm with some likely range of an hour, for example). The location indicator is detected when the user is located at a location where a meal is likely to be consumed (e.g., a restaurant). The blood glucose indicator is detected when the user's blood glucose level is below a predefined low-end threshold (e.g., a hypoglycemic state) or above a pre-defined high-end threshold (e.g., a hyperglycemic state). The position indicator is detected when the user is stationary and in a seated position. The photo indicator is detected when the user captures a photograph of food that the user is about to consume. The keyword indicator is detected when a user's calendar event indicates that the user is about to consume or is likely to consume a meal.

When a user is about to consume a meal, management of the diabetic condition includes providing mealtime alert to the user. The mealtime alert includes an indication for the user to perform management of the diabetic condition. For example, the mealtime alert may indicate for the user to take medication and/or vitamins, measure a pre- and/or post-meal blood glucose level associated with user, record an amount of carbs consumed by the user (e.g., or some dimension about a meal consumed by the user), use a bolus insulin calculator (e.g., to determine an amount of insulin to inject), inject a meal bolus of insulin, or recording a meal bolus insulin amount.

To assist in managing the diabetic condition, one or more user devices may be implemented to detect when the user is engaging in exercise or other elevated activity. The diabetic condition may be managed in response to an indication that the user is engaging in exercise or other elevated activity. An activity score is determined based on the detection of one or more activity indicators. The activity indicators include one or more of a heartrate indicator, a location indicator, and a keyword indicator. The heartrate indicator indicates an elevated blood flow and/or heartbeat of the user. The location indicator indicates a location of the user device associated with the user. A keyword indicator keyword indicator indicates when a user is scheduled to be performing an exercise.

The activity score is calculated based on the number of indicators that have been detected over a period of time. Each activity indicator provides additional context around the likelihood of an increased level of activity by the user. The activity score is used to determine the likelihood that user is exercising or otherwise engaging in an elevated activity. Management of the diabetic condition is performed proximate to a user exercising, for example, to increase the efficacy of management of the diabetic condition.

Management of the diabetic condition may be autonomously performed (e.g., without interaction from the user and/or with limited interaction from the user). For example, management of the diabetic condition is autonomously performed when a meal is about to be consumed by a user. Similarly, management of the diabetic condition is autonomously performed when a user is engaging in elevated activity. Autonomous management of the diabetic condition includes determining the basal rate of a user's insulin pump and delivering a meal bolus of insulin to the user. The more information about the individual that can be used to inform the insulin injections from an insulin pump, the greater the opportunity to optimize the insulin pump's operation.

DETAILED DESCRIPTION

Figure 1:
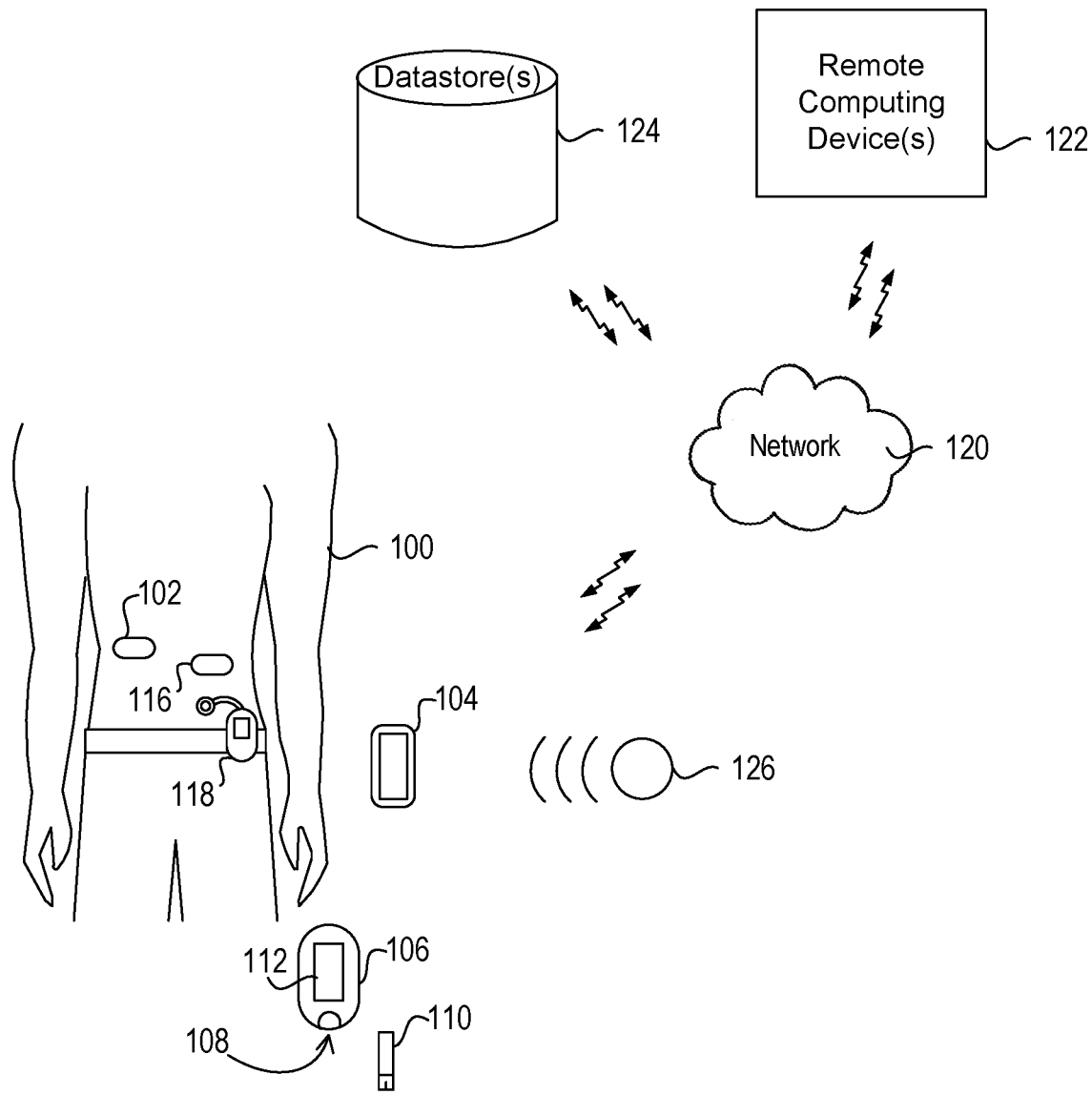
FIG. 1 is a perspective view of a representative environment for monitoring and/or treating a diabetic condition.

FIG. 1 is a perspective view of a representative environment for monitoring and/or treating a diabetic condition. As shown in FIG. 1, a user 100 with diabetes mellitus (referred to herein as diabetes) uses one or more devices to help monitor and/or treat the diabetic condition. The diabetic condition includes a metabolic syndrome, pre-diabetes, type 1 diabetes, type 2 diabetes, or gestational diabetes. The user 100 is in an extreme diabetic state, such as hypoglycemia or hyperglycemia, when the blood glucose level of the user 100 is below or above a threshold blood glucose level. The user 100 may use a blood glucose monitoring device to monitor blood glucose levels.

As used herein, the term "blood glucose monitoring device" refers to any device that detects and reports a level of glucose in the blood of the user, either through direct measurement of the blood or through an indirect detection process. A blood glucose level is also referred to as a blood sugar level. Examples of blood glucose monitoring devices include, but are not strictly limited to, continuous glucose monitoring devices, flash glucose monitoring devices, and blood glucose meters that provide a single measurement of blood glucose levels from a blood sample in a "spot" monitoring process. FIG. 1 depicts examples of blood glucose monitoring devices that are described in more detail below.

As used herein, the term "mobile device" refers to any mobile electronic device that is capable of moving with a user as the user changes locations. Example mobile devices include mobile phones, smartphones, wearable devices, tablets, laptops, notebook computers, personal digital assistants (PDAs), and any other mobile electronic device that is capable of moving with a user. Some embodiments of the mobile device incorporate the blood glucose monitor into an integrated device.

In some embodiments, the blood glucose monitoring device is a continuous glucose monitor (CGM) 102. The CGM 102 includes a subcutaneous sensor that is used to sense and monitor the amount of glucose in interstitial fluid of the user 100. As described herein, the amount of glucose in the interstitial fluid of the user 100 includes a blood glucose level. The CGM 102 includes a transmitting device that is located directly over the sensor that wirelessly powers the data transfer from the sensor. The CGM 102 periodically communicates data indicating the blood glucose levels of the user 100 to an external device, such as a mobile device 104, for computing and/or storing the blood glucose levels of the user 100. The mobile device 104 may operate as a CGM controller device. Though the mobile device 104 is provided as an example of a device with which the CGM 102 may communicate, the CGM 102 may communicate with other dedicated CGM controller devices for providing similar functionality that is described herein for the mobile device 104. The mobile device 104, or another CGM controller device, provides audible alerts, graphical user interfaces, or non-audible alerts in response to data indications or triggers identified in the monitored blood glucose data. The CGM 102 may include the sensor implanted in the user 100 and the transmitter, which may be applied to the body of the user 100. In one embodiment, the CGM 102 processes the blood glucose data for providing alerts. In another embodiment, the blood glucose data is processed at the mobile device 104, or other CGM controller device, and an alert indicator is communicated to the CGM 102.

In some embodiments, the blood glucose monitoring is performed by flash glucose monitoring (FGM). The FGM includes a subcutaneous sensor 103 that is used to sense and monitor the amount of glucose in interstitial fluid of the user 100. A separate reader device, such as the mobile device 102 or another reader device, receives the blood glucose information from the sensor when the device is within the RF range of the sensor 103. The sensor 103 transmits an instantaneous blood glucose level or a graphical trend of the blood glucose level to the reader device for display.

The user 100 may use a blood glucose meter (BGM) 106 as a blood glucose monitoring device to monitor blood glucose levels. The BGM 106 includes a port 108 that receives a blood glucose measurement strip 110. The user 100 may deposit a sample of blood on the blood glucose measurement strip 110. The BGM 106 analyzes the sample and measures the blood glucose level in the sample. The blood glucose level measured from the sample is displayed on a display 112 of the BGM 106 or communicated to an external device, such as the mobile device 104.

The blood glucose level measured by the BGM 106 or computed using data received from the CGM 102 is used to treat the diabetic condition of the user 100. For example, the user 100 may use an ambulatory non-durable insulin pump 116 or an ambulatory durable insulin pump 118 to treat the diabetic condition with insulin. The mobile device 104 determines an amount of insulin to be administered to the user 100 and the insulin pump 116, 118 receives instructions from the mobile device 104 to deliver a predetermined amount of insulin to the user 100. In some embodiments, the insulin pump 116, 118 receives other information from the mobile device 104, such as mealtime information or exercise information of the user 100. The insulin pump 116, 118 determines the amount of insulin to administer based on the received information from the mobile device 104. The insulin pump 116, 118 communicates information to the mobile device 104. The information communicated to the mobile device 104 includes an amount of insulin delivered to the user 100, corresponding times of delivery, or a pump status (e.g., battery status, insulin status, or another status of a portion of the pump).

The mobile device 104 communicates with the insulin pump 116, 118, the CGM 102, or the BGM 106 using wired or wireless communications. The mobile device 104, the CGM 102, a CGM controller, the BGM 106, or the insulin pump 116, 118 are collectively referred to as user devices. The mobile device 104 communicates with the other user devices using the same or different wireless protocols. For example, the mobile device 104 communicates with the other user devices using BLUETOOTH®, near field communication (NFC), THREAD®, WIFI®, ZIGBEE®, WI-MAX®, a cellular communication protocol, a proprietary wireless communication protocol, or another radio frequency (RF) communication protocol.

In some embodiments, the mobile device 104 is a mobile phone, a tablet, a laptop, a wearable device, a personal digital assistant (PDA), or another mobile computing device. If the mobile device 104 is a wearable device, the wearable device may be an armband (e.g., a smart watch, such as an APPLE® watch, a FITBIT® armband, or other device capable of being worn on the arm of the user 100), a ring, glasses (e.g., GOOGLE® GLASS™), a headset (e.g., BLUETOOTH® headset), clothing (e.g., shirts, gloves, or another article of clothing), or another wearable device capable of being worn by the user 100. The mobile device 104 may include an electric motor for providing on-body vibration alerts and/or a speaker for providing audible alerts in response to data indications or triggers identified in the monitored blood glucose data. Though a mobile device is described herein, other computing devices may be similarly implemented to perform functions of the mobile device 104.

The mobile device 104 receives data and store data for assisting in monitoring or treating the diabetic condition. The mobile device 104 may receive input from the user 104 via a user interface being provided on a display. The mobile device 104 receives input via hard buttons or soft buttons provided on the display.

In some embodiments, the mobile device 104 is configured to determine the device's location. For example, the mobile device 104 is able to determine the geolocation (e.g., latitude and longitude) of the device using signals from a global positioning system (GPS) or triangulation via cellular communications. In some embodiments, the mobile device 104 determines a relative location using an RF beacon device 126. The RF beacon device 126 communicates a unique identifier via a short-range wireless communication, such as a BLUETOOTH® low energy (BLE) beacon or an NFC beacon. The mobile device 104 receives the RF beacon and performs a lookup in a database (e.g., in information from the datastores 124) to determine a relative location associated with the unique identifier. For example, the mobile device 104 determines that the RF beacon indicates that the device is in a particular room in a home or building, on a certain floor in a building, close to a predefined object, or is within the RF range of a beacon associated with another object or location. The RF beacon device 126 may be used for determining the geolocation of the mobile device 104, for example, using WIFI® positioning systems (WPS) or WiPS/WFPS.

The mobile device 104 includes one or more sensors for detecting a relative position of the device or information about the user 100. The mobile device 104 detects a movement or a change in orientation. Based on the movement or change in orientation (or lack thereof) of the mobile device 104 over a period of time, the mobile device 104 detects that the user 100 is standing, sitting, or lying down. The mobile device 104 detects that the user 100 is exercising when the movement or the change in orientation is greater than a threshold for a period of time. The mobile device 104 detects the heartrate of the user 100 using a heartrate sensor. Based on the heartrate and the movement of the user 100 over a period of time, the mobile device 104 detects whether the user 100 is asleep or awake. The information about the mobile device 104 or the user 100 is used to provide information about or treat the diabetic condition.

The mobile device 104 provides information to the user 100 about the user's diabetic condition. For example, the mobile device 104 provides blood glucose levels, provides meal-related information, provides exercise-related information, generates graphs and other graphical user interfaces for display, or generates alerts that are provided to the user 100. For example, the mobile device 104 measures the blood glucose level of the user 100 and provides an alert when the blood glucose level of the user 100 has reached a threshold for an extreme diabetic state (e.g., hypoglycemia or hyperglycemia). The alerts provided by the mobile device 104 are audible or non-audible alerts. The non-audible alerts are provided as a vibration, a flashing of the screen, or a flashing of an LED on the mobile device 104. In some embodiments, the alerts are also, or alternatively, provided by an external device based on a communication from the mobile device 104.

The mobile device 104 communicates with other devices directly via a wired communication or a short-range wireless communication (e.g., WI-FI®, BLUETOOTH®, BLE, NFC, or another short-range wireless communication). The mobile device 104 communicates indirectly with remote computing devices 122 or datastores 124 via a network 120 (e.g., using a WI-FI® network, a cellular network, a WI-MAX® network, or another wired or wireless network). The network 120 is a wired or wireless network. The network 120 is used to communicate over the Internet to other devices.

The mobile device 104 communicates with the remote computing devices 122 to generate user interfaces for display on the mobile device 104, perform remote computation, or otherwise control a remote computing device. For example, the mobile device 104 provides a user interface via an application or web browser that is generated at a remote computing device 122. The mobile device 104 generates instructions for providing alerts via remote computing devices 122 based on information received from the user 100, the CGM 102, the BGM 106, or the insulin pump 116, 118. Example remote computing devices 122 to which the mobile device 104 sends communications for performing alerts include a remote computer (e.g., a server, a laptop, or other computer), an external speaker, an external display device (e.g., television, monitor, or another device having an external display), a home automation system, a remote telecommunications device (e.g., for sending text or voice communications to an emergency contact over a telecommunications network), a home appliance (e.g., refrigerator), or another remote computing device.

The mobile device 104 communicates with the datastores 124 to store information or retrieve information. The information includes information related to the user 100, the CGM 102, the BGM 106, or the insulin pump 116, 118. For example, the mobile device 104 receives treatment information associated with the user 100 as input or receive blood glucose information from the CGM 102 or the BGM 106 and send the information to the datastores 124 via the network 120. Stored information is retrieved from the datastores 124 for treatment of the diabetic condition of the user. For example, the mobile device 104 retrieves an amount of insulin delivered to the user 100 or corresponding times of delivery. The datastores 124 include one or more remote storage locations, which are collectively referred to as cloud storage.

The user 100 may be diagnosed with the diabetic condition and may enter an extreme diabetic state if the user 100 is unable to properly manage the diabetic condition proximate to the consumption of a meal. To assist in managing the diabetic condition, the user 100 receives alerts via a user device. For example, one or more user devices may be implemented to detect when a meal is to be consumed and/or is likely to be consumed by the user. The diabetic condition is managed in response to an indication that a meal is to be consumed and/or is likely to be consumed by the user by performing one or more actions via a user device. The diabetic condition is managed by alerting the user 100 to take medication, measure a pre- or post-meal blood glucose level, record the amount of carbs consumed by the user 100, record dimension about a meal consumed by the user 100, use a bolus insulin calculator (e.g., to determine an amount of insulting to inject), inject a meal bolus of insulin, or recording a meal bolus insulin amount.

The user 100 may enter an extreme diabetic state if the user 100 is unable to properly manage the diabetic condition proximate to engaging in exercise or other elevated activity. To assist in managing the diabetic condition, one or more user devices are implemented to detect when the user is engaging in exercise or other elevated activity, or is likely to be engaging in exercise or other elevated activity. The diabetic condition is managed in response to an indication that the user is engaging in exercise or other elevated activity, or is likely to be engaging in exercise or other elevated activity, by performing one or more actions via a user device.

Figure 2:
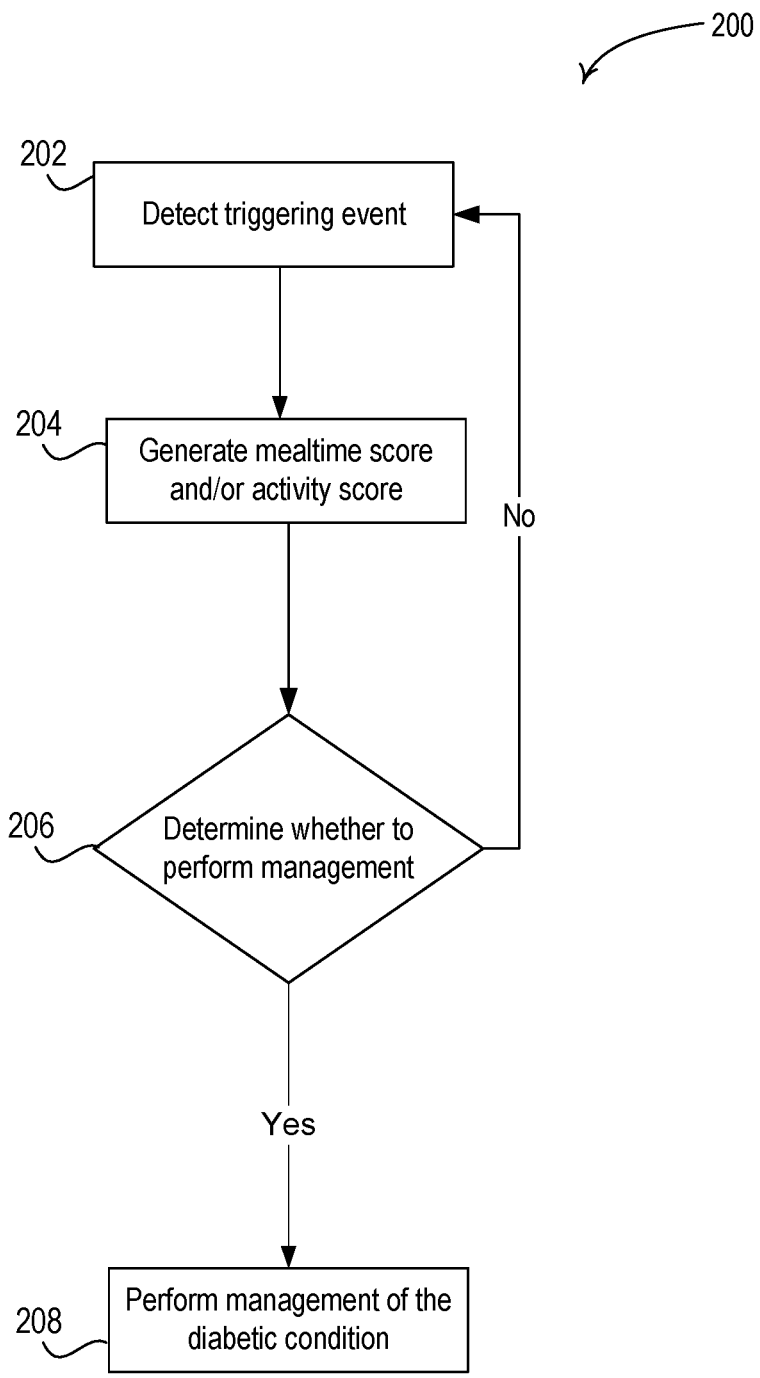
FIG. 2 illustrates an example procedure for performing management of a diabetic condition via one or more user devices.

FIG. 2 illustrates an example procedure 200 for performing management of the diabetic condition via one or more user devices. The procedure 200 may be performed by a single user device (e.g., a mobile device, a CGM controller, a BGM, an insulin pump, or another user device) or distributed across multiple user devices. The procedure 200 may also, or alternatively, be implemented using another computing device, such as remote computing device, for example.

As illustrated in FIG. 2, one or more scores are generated that indicate a likelihood that an action is to be performed to assist the user in managing the diabetic condition. At 202, a triggering event is detected for generating the one or more scores that indicate a likelihood that an action is to be performed to assist the user in managing the diabetic condition. For example, a triggering event may be detected in response to an indication that a predefined meal-time is occurring, is to occur within a period of time, or a period of time has elapsed since a last mealtime. The triggering event may be detected in response to a keyword indicator from a prestored event associated with the user indicating the occurrence of a mealtime, exercise, or other elevated activity. The triggering event may be detected in response to a photograph indicator generated in response to a photograph of food or a photograph of an activity being taken by a user device. The triggering event may be detected in response to a location indicator that indicates a location where a meal is likely to be consumed or the user is likely to exercise. The triggering event may be detected in response to a blood glucose indicator indicating that a blood glucose level of the user is above a high-end threshold (e.g., hyperglycemic or trending toward being hyperglycemic) or below a low-end threshold (e.g., hypoglycemic or trending toward being hypoglycemic). The triggering event may be detected in response to a heartrate indicator indicating an elevated heartrate of the user. The triggering event may be detected in response to a position indicator indicating a change in the user's position (e.g., sitting, standing, or lying down). Each mealtime indicator provides additional context around the likelihood of a mealtime. Each activity indicator provides additional context around the likelihood of an increased level of activity by the user.

At 204 a mealtime score or an activity score is generated based on information received at a user device. The mealtime score is generated based on the detection of one or more mealtime indicators. An activity score may indicate the likelihood that the user is exercising, has exercised, or will imminently exercise. An activity score is determined based on the detection of one or more activity indicators. The scores may continue to be generated over a period of time from the initial triggering event detected at 202. As additional indicators are detected, the respective scores increase, which indicates and increased likelihood that the user is approaching a mealtime or exercising.

The mealtime indicators or activity indicators are associated with respective weights to determine the corresponding scores. The weight associated with a mealtime indicator indicates the likelihood that a user is consuming, has consumed, or will imminently consume a meal based on the indicator. The weight associated with an activity indicator indicates the likelihood that a user is exercising or performing an elevated activity. The respective weights of the mealtime indicators are summed together to determine the mealtime score. The respective weights of the activity indicators are summed together to determine the activity score.

At 206, a determination is made as to whether to perform management of the diabetic condition. The determination at 206 is based on the mealtime score and the activity score. For example, management of the diabetic condition may be performed when the mealtime score is above a predefined threshold. The threshold indicates whether a threshold number of mealtime indicators have been detected. The threshold is configured (e.g., pre-configured or configured by the user) based on a desired level of confidence that a mealtime has occurred, is occurring, or is about to occur. The greater the threshold for the mealtime score, the higher the confidence level that the mealtime has occurred, is occurring, or will occur.

The determination at 206 is based on the activity score. For example, management of the diabetic condition may be performed when the activity score is above a predefined threshold. The threshold is used to indicate whether a threshold number of activity indicators have been detected. The threshold is configured (e.g., pre-configured or configured by the user) based on a desired level of confidence that exercise or an increased level of activity has occurred, is occurring, or is about to occur. The greater the threshold for the activity score, the higher the confidence level that the exercise or an increased level of activity has occurred, is occurring, or will occur.

If, at 206, it is determined that management of the diabetic condition is to be performed, management of the diabetic condition is performed at 208. As described herein, management of the diabetic condition includes providing mealtime alerts to the user and controlling a basal rate of the user's insulin pump. The form of management of the diabetic condition performed may depend on the relevance (e.g., the contextual relevance) of the detected mealtime indicator(s), the relevance (e.g., the contextual relevance) of the detected activity indicators, the mealtime score, and/or the activity score. For example, the detection of certain triggering event results in certain forms management of the diabetic condition being performed.

Figure 3A:
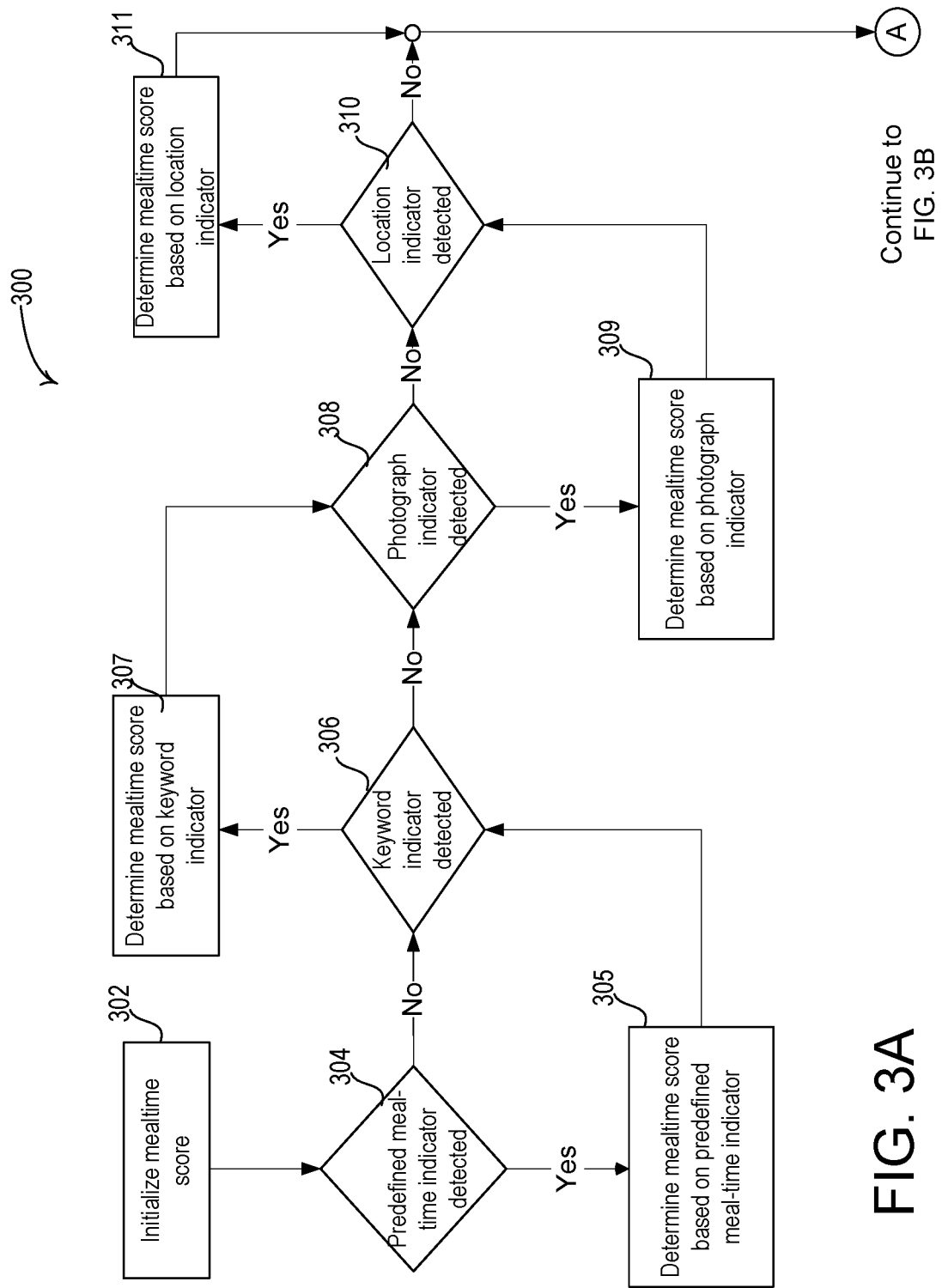
FIGS. 3A and 3B are flow diagrams illustrating an example procedure for determining a mealtime score.
Figure 3B:
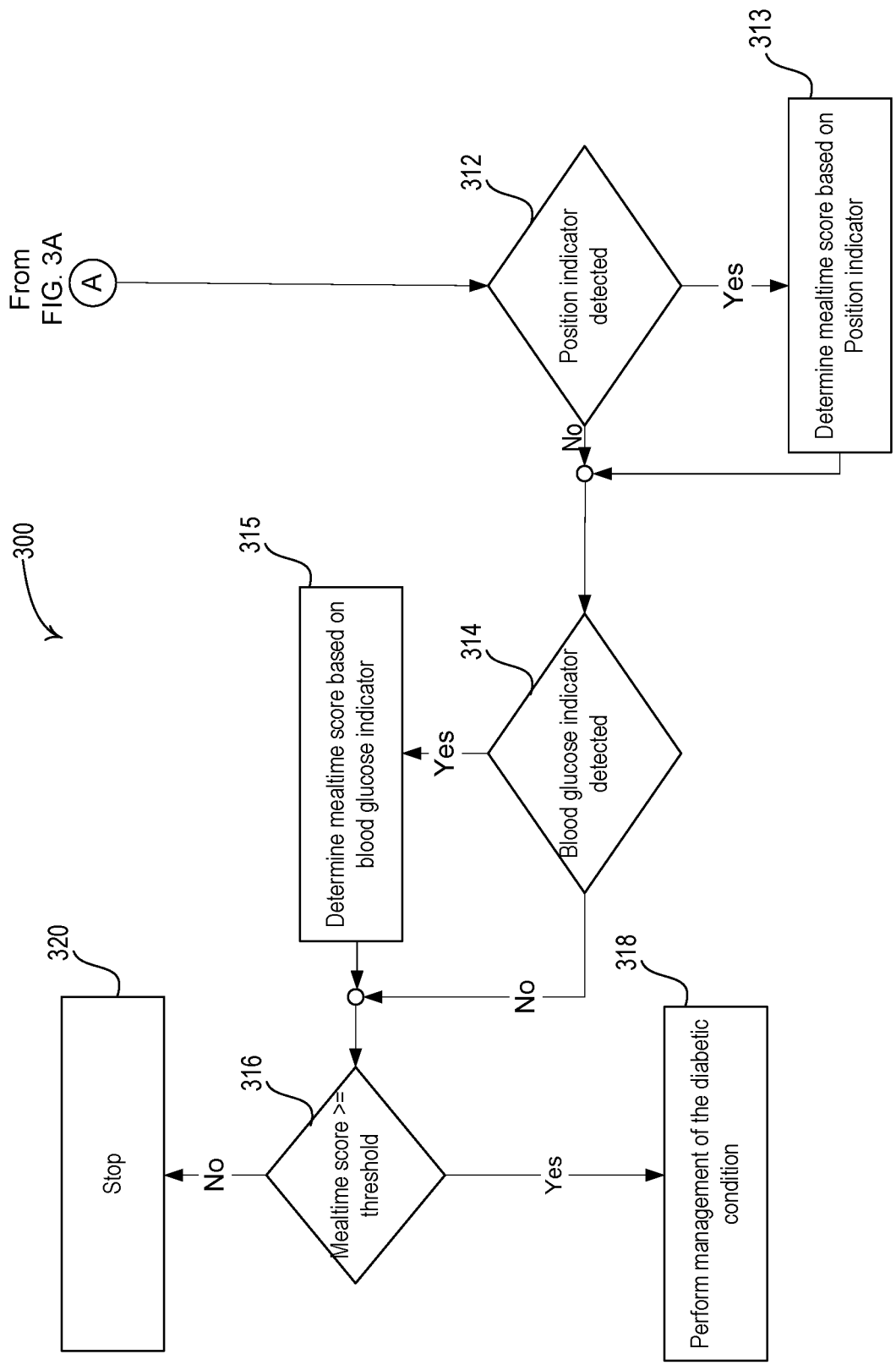

FIGS. 3A and 3B illustrate a flow diagram of an example procedure 300 to determine a mealtime score. As described herein, the procedure 300 is performed in conjunction with the procedure 200. The procedure 300 may be performed by a single user device (e.g., a mobile device, a CGM controller, a BGM, an insulin pump, or another user device) or distributed across multiple user devices. The procedure 300 may also, or alternatively, be implemented using another computing device, such as remote computing device, for example.

As shown in FIG. 3A, a mealtime score is determined based on the detection of one or more mealtime indicators. The mealtime indicators include a predefined meal-time indicator, a location indicator, a position indicator, a blood glucose indicator, a photograph indicator, and a keyword indicator. The mealtime score is calculated based on the number and context of indicators that have been detected over a period of time. The mealtime score is used to determine the likelihood that user has consumed, is about to consume, or is consuming a meal. The mealtime score is determined with or without input from the user. As described herein, management of the diabetic condition is performed proximate to the consumption of a meal, for example, to increase the efficacy of management of the diabetic condition. Automated detection and/or alerts prevents the user from failing to perform management of the diabetic condition proximate to the consumption of meal (e.g., because the user may forget).

At 302, the mealtime score is initialized (e.g., the mealtime score is set to zero). The mealtime score may be initialized after: receiving an indication to initialize the mealtime score from a user, a predefined period of time after a prior mealtime, or upon an initial execution of an application on the user device.

At 304, a predefined mealtime indicator may be detected. The pre-defined mealtime indicator is detected at estimated meal times associated with the user. The estimated mealtimes include the times when certain meals (e.g., breakfast, lunch, and/or dinner) are likely to be consumed by the user. For example, the estimated mealtimes may include: 7 am to 10 am, 12 pm to 2 pm, and 6 pm to 8 pm. The estimated mealtimes may be defined by a user (e.g., user defined mealtimes). For example, the user inputs the estimated mealtimes via a user device (e.g., mobile device 104 or remote computing device 122).

Estimated mealtimes may be updated over time. For example, the estimated mealtimes may be updated based on a detection that a meal has been eaten or is likely to be eaten by the user. The meal detection times are stored and tracked over time, for example, via a user device. The estimated mealtimes may be updated and adjusted based on the stored meal detection times. For example, the estimated mealtimes are updated when the mealtime score is above a predefined threshold at a time that is outside of the currently predefined mealtimes. The estimated mealtimes are updated after a certain number of mealtimes are detected outside of the current estimated mealtimes (e.g., three times in the last week).

If the predefined mealtime indicator is detected at 304, the mealtime score is determined based on the predefined mealtime indicator at 305. For example, the mealtime score is increased by the predefined meal-time indicator weight. The weight of each mealtime indicator may be equal, or the mealtime indicators may be weighted differently based on the importance of a given indicator in predicting a mealtime of the user. For example, each meal-time indicator weight includes an equal value (e.g., a value of one) and the more indicators that are detected increase the likelihood that a mealtime is detected. In another example, meal-time indicators that provide a greater likelihood of meal consumption are given a greater weigh, such as the location of the user device being given a greater weight than a predefined mealtime.

Additional meal-time indicators may be used to calculate the mealtime score. For example, a keyword indicator may be detected at 306. The keyword indicator is detected based on information in a user's calendar. The user's calendar may be stored locally or accessed remotely (e.g., in a datastore or remote computing device) via a calendar service at a user device.

The user's calendar includes one or more pre-scheduled events, which describes the user's scheduled activity at a certain time. The calendar events are searched for certain keywords (e.g., using keyword mining). The keywords are analyzed within certain fields associated with the event, such as the title, the location, or the description. For example, the keywords may include one or more meal-related words that are associated with meal consumption, such as lunch, dinner, eat, or restaurant. The keyword indicator is triggered or detected when a meal-related word is found within a user's calendar event.

The keywords include one or more meal-related locations. The location of a pre-scheduled event is cross referenced with a list of locations where meals are likely to be consumed (e.g., a restaurant, a cafeteria, or another location). For example, the location may be looked up from a dataset of locations stored locally on the device or accessed remotely from a datastore or remote computing device. When the location of a pre-scheduled event matches a location where meals are consumed (e.g., a restaurant, a cafeteria, or another location), a keyword indicator is detected. The location may also be stored with a location type or name of the establishment that may indicate the establishment is a location where meals are consumed (e.g., a restaurant, a cafeteria, or another location).

If the keyword indicator is detected at 306, the mealtime score is determined based on the keyword indicator at 307. For example, the mealtime score is increased by the keyword indicator weight. The keyword indicator weight may be based on the keyword mined and/or the number of keywords found during keyword mining. For example, if three keywords are found during keyword mining, the keyword indicator weight includes a value of three. If the keyword identified is a stronger indicator of a mealtime activity, the weight is increased. Although the examples provided herein refer to a calendar event for detecting keywords, the keyword indicator is detected based on any event planning or scheduling medium (e.g., a social media profile of the user).

A photograph indicator may be detected at 308. A user captures a photograph, for example, via a user device. The photograph is processed to determine if food is present in the photograph (e.g., a food photograph is captured by the user). For example, the processing includes detecting the presence of a plate or food from within the photograph. The processing considers the angle at which the image was captured. The processing includes examining the exchangeable image file format metadata associated with a photograph. The metadata (e.g., the SubjectDistance metadata) may indicate the distance between the device capturing the image (e.g. the mobile phone 104) and the subject of the photograph. The metadata may indicate the angle at which the photograph is captured. For example, food photograph that is captured from a predefined distance (e.g., 1 to 3 feet) and/or a predefined angle (e.g., a downward angle) indicate that a meal is likely to be consumed and may trigger detection of the photograph indicator.

A photograph captured by a user is compared to one or more prestored images to determine if food is present in the photograph. The prestored images include food photographs. The photograph captured by the user are processed to determine a similarity between the photograph and the prestored images. For example, the processing may include the detection of: certain textures or patterns; the spatial density of items in the photograph (e.g., in the center of the photograph); the plate shape against the table background; and/or the height or volume of an object in the photograph. If the similarity between the photograph captured by the user and a prestored image are above a threshold, the photography indicator is detected. The image processing may be performed using a photo service, which may include a neural network image classifier capable of identifying various types of food that have been learned from prestored images.

If the photograph indicator is detected at 308, the mealtime score is determined based on the photograph indicator at 309. For example, the mealtime score is increased by the photograph indicator weight. The photograph indicator weight may include a value of one. The photograph indicator weight includes a value dependent on the level of confidence that the photo includes a meal-related item. For example, detection of a plate may have a lower weight than detection of food. The number of similarities between the image and the prestored images informs the level of confidence that the photo includes a meal-related item, and the greater the level of confidence causes the photograph indicator to have a higher weight value.

A location indicator may be detected at 310. For example, the GPS location of a user is sensed or received, and used to determine the user's current location. For example, the user's GPS location is sensed and/or received at a user device (e.g., the mobile phone 104). The user's GPS location indicates a latitude and a longitude that defines the user's current location. The latitude and longitude may be mapped to a physical address.

The physical address may be cross referenced with a list of locations (e.g., stored locally on a user device, or remotely at a datastore or remote computing device) where a meal is likely to be consumed. The list of locations where a meal is likely to be consumed is based on a list of businesses that includes the businesses' location. The list of business may be associated with metadata that includes information about the business (e.g., business type, business category, a sub-type). The metadata is processed to determine a list of businesses where a meal is likely to be consumed (e.g., a restaurant, a canteen, or a cafeteria). When the user's GPS location indicates that the user is currently located at a business and/or location where a meal is likely to be consumed, the location indicator is detected.

The location of the user may also, or alternatively, be identified using a short-range RF communication or input from the user on the user device. Short-range RF communications include a BLE beacon or other identifier that is received via an RF signal. The identifier is similarly cross-referenced with the identifier of a list of businesses, vending machines, or other locations that serve food. The list of locations includes an indication of a location type or a location category. The data from the list of locations is processed to determine whether the received identifier identifies a location where a meal is likely to be consumed (e.g., a restaurant, canteen, coffee shop, cafeteria, or a vending machine). The title of the location is similarly analyzed to determine whether the received identifier identifies a location where a meal is likely to be consumed. The user may also indicate a location of the device on the user device (e.g., on a virtual map) and an identifier associated with the location indicated by the user is analyzed to similarly determine whether the received identifier identifies a location where a meal is likely to be consumed.

The mealtime score is determined based on the location indicator at 311. For example, the mealtime score is increased by the location indicator weight. The location indicator weight may include a value of one. The weight of the location indicator is adjusted based on the confidence that the location of the user identifies a location where a meal is likely to be consumed. For example, a higher weight may be given to a restaurant than to a coffee shop.

Referring now to FIG. 3B, the position indicator may be detected at 312. The position indicator is used to determine that meal is to be consumed or is likely to be consumed. A user device includes an accelerometer and/or a gyroscope, which is used to determine the movement, position, and/or orientation of the user. From the information received from the accelerometer and/or gyroscope, the user device determines that the user is stationary and in a seated position. Meals may be consumed while a user is stationary (e.g., standing) or in a seated position. Accordingly, the position indicator is triggered or detected when the user's current location is stationary, and/or the user device indicates that the user is in a seated position.

If the position indicator is detected at 312, the mealtime score is determined based on the position indicator at 313. For example, the mealtime score is increased by the position indicator weight. The position indicator is weighted more heavily than other indicators, as the position indicator is a more reliable indicator of whether the user is eating. For example, the position indicator may be weighted at a value of two. The weight of the position indicator is adjusted based on the confidence level of the position indicator. For example, if the user is standing and stationary, the position indicator is given a lower weight than when the user is sitting and stationary.

At 314, the blood glucose indicator may be detected. A user's glucose level may be sensed or received from a user device (e.g., a wearable device, a blood glucose monitoring device, or the mobile phone 104). A low blood glucose level indicates that the user has not recently consumed a meal or that a meal is likely to be consumed. A high blood glucose indicates that a user has consumed a meal, although other factors may affect blood glucose levels. The blood glucose indicator is triggered or detected when the user's blood glucose level is above a high-end threshold or below a low-end threshold. The high-end and low-end thresholds vary based on the user. For example, the low-end threshold may include 70 mg/dl for a user. Similarly, the high-end and low-end thresholds vary over time. For example, the high-end threshold may vary from 130 mg/dl to 160 mg/dl based on an amount of time since a meal was last consumed by a user.

If the blood glucose indicator is detected at 314, the mealtime score is determined based on the blood glucose indicator at 315. For example, the mealtime score is increased by the blood glucose indicator weight. The blood glucose indicator weight may include a value of one. The weight of the blood glucose indicator is adjusted based on the blood glucose level. For example, the higher or lower the blood glucose level is from a predefined blood glucose level, the higher or lower, respectively, the weight assigned to the blood glucose indicator.

Although the procedure 300 is described as detecting the various mealtime indicators sequentially in a particular order and determining the mealtime score after the mealtime indicators have each been detected, the mealtime score may be determined or adjusted in numerous ways. For example, as illustrated in FIGS. 3A and 3B, the mealtime score may be determined after detecting any one or more of the described mealtime indicators and their respective context in any combination. The precise order of the operations illustrated in FIGS. 3A and 3B from 304-315 is shown for illustrative purposes. The operations performed from 304-315 may occur in any order, or in parallel. The mealtime score may be determined or calculated (e.g., updated) after each of the mealtime indicators have been detected, or after the selected group of indicators has been detected. Each mealtime indicator may be weighted similarly to any other mealtime indicator, or differently from any other mealtime indicator. For example, the mealtime score may be higher when the position indicator and the photograph indicator are detected, as compared to when the keyword indicator and the predefined meal-time indicator are detected.

The mealtime score is compared to a threshold at 316. For example, the mealtime score is compared to the threshold, at 316, a predefined period of time after an initial mealtime indicator is received. If the mealtime score is greater than or equal to a threshold, management of the diabetic condition is performed at 318. For example, the mealtime score may be greater than or equal to the threshold of three and management of the diabetic condition is performed at 318. If the mealtime score is less than the threshold, the process 300 stops at 320.

Management of the diabetic condition includes providing mealtime alerts to the user via a user device. The mealtime alert may be audible, a vibration, visually displayed on the user device, and provided via an external device. The mealtime alert may indicate that the user should monitor the user's blood glucose level. The mealtime alert may indicate that the user should use a bolus calculator, such as the bolus calculator on the mobile device or an external bolus calculator, to calculate the recommended amount of insulin to take, which triggers the user to estimate and/or log an amount of carbs consumed. The mealtime alert may indicate that the user should monitor the user's blood glucose level, record an amount of carbs consumed, or deliver a bolus. The mealtime alert may display an alert to the user to indicate that the user should open an application, or the mealtime alert may automatically open the application. The application may allow the user to calculate a bolus, enter the user's blood glucose level, display the user's blood glucose level (e.g., entered or automatically detected blood glucose level), record and display an amount of insulin consumed, or record the amount of carbs consumed.

Management of the diabetic condition may be performed prior to a user consuming a meal. For example, management of the diabetic condition includes providing mealtime alerts to assist the user in reducing a body mass index (BMI) of a user diagnosed with the diabetic condition. Accordingly, a mealtime alert is provided to a user (e.g., prior to the user consuming a meal) that indicates for the user to: take smaller bites, chew a certain number of times (e.g., 42 times) before swallowing, not take an additional serving of the meal, stop eating the meal when the user feels full, pause during eating to determine if the user is full.

Management of the diabetic condition may be performed after a user consumes a meal. Accordingly, management of the diabetic condition includes providing a mealtime alert to a user after the user consumes a meal. For example, a mealtime alert may be provided at one or more of the following instances. A mealtime alert may be provided to the user after a period of time (e.g., ten minutes) since the user was determined to consume a meal. A mealtime reminder may be provided to the user after a period of time (e.g., forty minutes) since the user recorded information about a meal (e.g., via a user device). A mealtime alert may be provided to the user after a period of time (e.g. forty minutes) since the user calculated a recommended bolus insulin amount. A mealtime alert may be provided to the user after a period of time (e.g. forty minutes) since the location indicator was triggered. A mealtime alert may be provided to the user after a period of time (e.g. forty minutes) since the position indicator was detected. A mealtime alert may be provided to the user when the user is in an extreme diabetic condition (e.g., when the user quickly transitions to a hyperglycemic or hypoglycemic state).

Management of the diabetic condition may be performed prior to a user consuming a meal. For example, management of the diabetic condition includes providing alerts (e.g., subsequent to the user consuming a meal) to assist the user. Accordingly, the mealtime alert may include one or more of the following indications. The mealtime alert may indicate to the user to test the user's blood glucose level (e.g., via a user device). The mealtime alert may indicate to the user to apply an insulin bolus (e.g., a correction meal bolus). The mealtime alert may indicate to the user to track information about a meal consumed by the user.

As described herein, the mealtime alerts are provided on a user device closer to an actual mealtime of a user. Similarly, the activity alerts are provided on the user device closer to when the user is actually performing an activity. Providing such diabetes-related alerts closer to the time at which a user may notice the alerts prevents the user device, which may be a diabetes monitoring and/or treatment device with limited battery capacity, from utilizing processing power and battery power unnecessarily by providing alerts. For example, the user device may provide fewer alerts to the user, because the level of confidence in the mealtime or time of the activity of the user is higher when based on the mealtime score and/or the activity score. The user device also avoids generating alerts that go unrecognized, as the alerts are generated at a time that is proximate the mealtime or activity.

Figure 4:
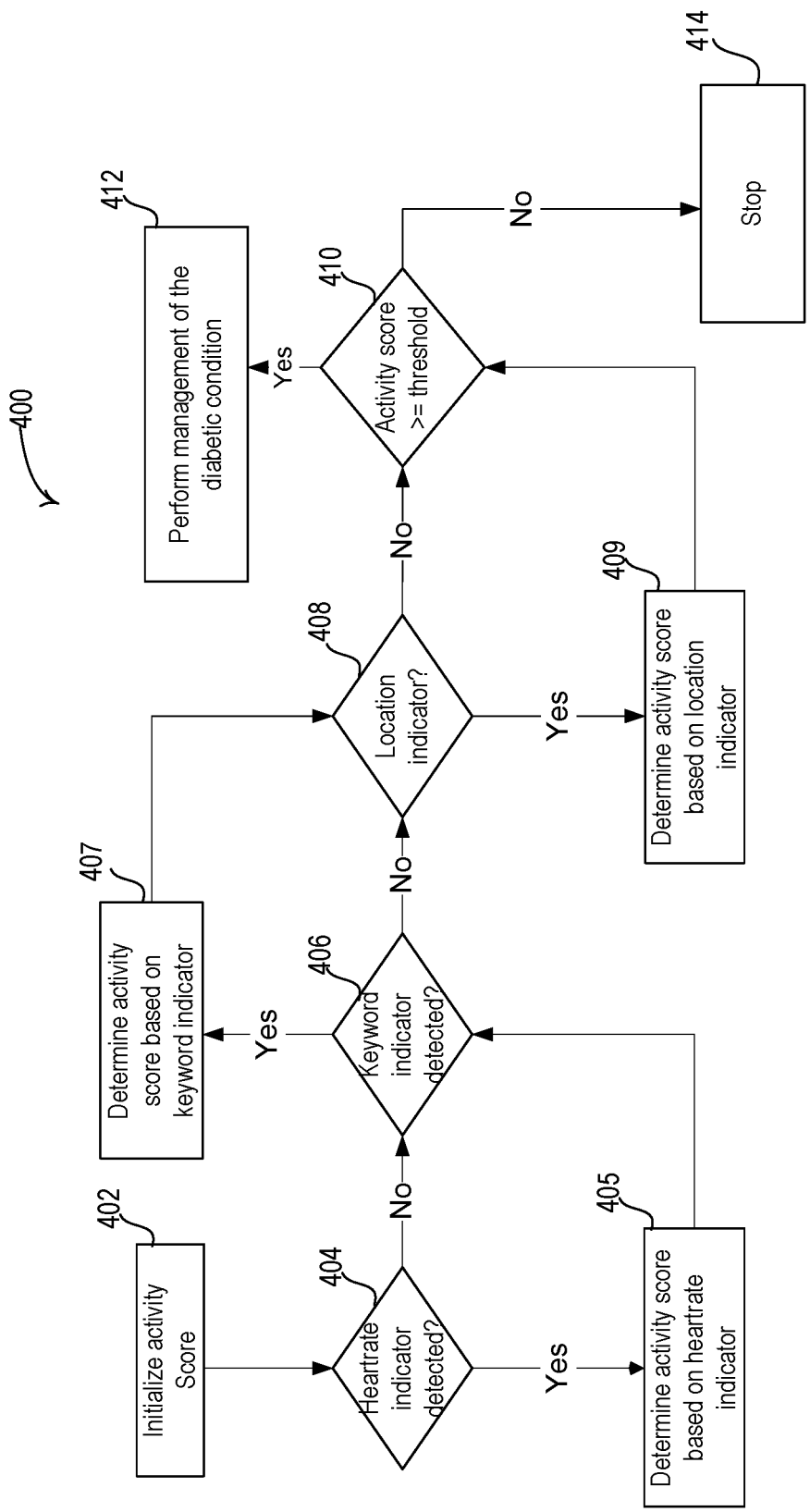
FIG. 4 is a flow diagram illustrating an example procedure for determining an activity score.

FIG. 4 illustrates a flow diagram of an example procedure 400 for determining an activity score. As described herein, the procedure 400 is performed in conjunction with the procedure 200. The procedure 400 may be performed by a single user device (e.g., a mobile device, a CGM controller, a BGM, an insulin pump, or another user device) or may be distributed across multiple user devices. The procedure 400 may also, or alternatively, be implemented using another computing device, such as remote computing device, for example.

As illustrated in FIG. 4, an activity score is determined based on the detection of one or more activity indicators. The activity indicators include a heartrate indicator, a location indicator, and/or a keyword indicator. The heartrate indicator indicates an elevated blood flow or heartbeat of the user. The location indicator indicates a location of the user device associated with the user. A keyword indicator keyword indicator indicates when a user is scheduled to be performing an exercise. The activity score is calculated by based on the number and context of indicators that have been detected over a period of time. The activity score is used to determine the likelihood that user is exercising. Management of the diabetic condition may be performed proximate a user exercising, for example, to increase the efficacy of management of the diabetic condition. However, a user may not perform management of the diabetic condition proximate to exercising (e.g., because the user may forget).

At 402, the activity score is initialized (e.g., set to zero). The activity score may be initialized after one or more of the following instances: receiving an indication to initialize the activity score from a user, a predefined period of time after a prior workout or other activity, or upon an initial execution of an application on the user device.

The heartrate indicator may be detected at 404. The heartrate indicator is detected at a user device (e.g., a mobile phone, a wearable device, a heartrate monitor, or another user device). The user device includes a heartrate monitor, which is used to sense the user's heartrate, or other sensors to detect blood flow. The user device compares the user's current heartrate or blood flow to a threshold. If the user's current heartrate and/or blood flow is above the threshold, the heartrate indicator is detected.

The heartrate indicator is detected based on a change in the acceleration or orientation of a user device associated with the user. For example, the user device includes an accelerometer or a gyroscope, which is used to sense the user's current activity (e.g., running, climbing, or another activity). If the user device detects elevated level of activity (e.g., greater than a threshold), the heartrate indicator is detected.

The user device tracks user activity levels, such as the user's heartrate, blood flow, or activity levels to determine a deviation from a normal. For example, the user's previous heartrate, blood flow, or activity levels is stored on the user device or another device (e.g., an external device 122 and/or datastores 124). The user's current activity levels are compared the user's previous activity levels to determine if the user's current activity level is elevated. If the user's current activity level is above the user's previous activity levels, the heartrate indicator is detected.

If the heartrate indicator is detected at 404, the activity score is determined based on the heartrate indicator at 405. For example, the activity score is increased by the heartrate indicator weight at 405. The heartrate indicator weight may include a value of one. The heartrate indicator weight is adjusted based on the level of activity detected by the heartrate indicator. For example, the weight of the heartrate indicator may be greater when the heartrate or blood flow of the user is higher.

A keyword indicator may be detected at 406. The keyword indicator is detected based on a user's calendar or other event planning or scheduling medium (e.g., a social media profile of the user), which may be accessed via a user device (e.g., the mobile device 104 or the external device 122). The user's calendar includes one or more pre-scheduled events, which describes the user's scheduled activity at a certain time. The calendar events are searched for certain keywords (e.g., keyword mining). The keywords are searched for from within certain fields associated with the event (e.g., title, location, or description). For example, the keywords include one or more activity-related words that are associated with an exercise activity, such as, for example: gym, exercise, running, or basketball. The keyword indicator is triggered or detected when one or more activity-related words associated with exercise are found within a user's calendar event.

The location of pre-scheduled event may be cross referenced with a list of locations where user activity (e.g., exercise) is likely to occur (e.g., a gym, a park, or another location). The location includes the name of a pre-recognized exercise facility in the list of locations. The list of locations may be stored locally on the user device or accessed remotely from a remote computing device or datastore. The keyword indicator is triggered or detected when the user's calendar indicates that the user is at a location where exercise is likely to occur.

If the keyword indicator is detected 406, the activity score is determined based on the keyword indicator at 407. For example, the activity score is increased by a keyword indicator weight. The keyword indicator weight is based on the keyword mining and/or the number of keywords found during keyword mining. For example, if three keywords are found during keyword mining, the keyword indicator weight include a value of three. If the keyword identified is a stronger indicator of an exercise activity, the weight is increased.

The location indicator may be detected at 408. For example, the GPS location of a user is sensed or received, which is used to determine the user's current location. For example, the user's GPS location is sensed or received from a user device (e.g., the mobile phone 104). The user's GPS location indicates a latitude and a longitude to describe the user's current location.

The longitude and latitude are mapped to a physical address. The physical address is cross referenced with a list of locations where user activity (e.g., exercise) is likely to occur. The list of locations where user activity is likely to occur is based on a list of businesses, which may include the businesses' location. The list of business may be associated with metadata (e.g., business type, business category, a subtype). The metadata is processed to determine a list of businesses where increased user activity is likely to occur (e.g., a gym, a park, or another location). When the user's GPS location indicates that the user is currently located at a business or location where increased user activity is likely to occur, the location indicator is detected.

The location of the user may also, or alternatively, be identified using a short-range RF communication or input from the user on the user device. Short-range RF communications include a BLE beacon or another identifier that is received via an RF signal. The identifier is similarly cross-referenced with the identifier of a list of businesses or other locations at which increased user activity (e.g., exercise) is performed. The list of locations may include an indication of a location type or a location category. The data from the list of locations is processed to determine whether the received identifier identifies a location where exercise is likely to occur (e.g., a gym, a park, or another location). The title of the location is similarly analyzed to determine whether the received identifier identifies a location where exercise is likely to occur. The user also indicates a location of the device on the user device (e.g., on a virtual map) and an identifier associated with the location indicated by the user is analyzed to similarly determine whether the received identifier identifies a location where exercise is likely to occur.

If the location indicator is detected at 408, the activity score is determined based on the location indicator at 409. For example, the activity score is increased by the location indicator weight. The location indicator weight may include a value of one. The weight of the location indicator is adjusted based on the confidence that the location of the user identifies a location where higher levels of exercise is likely to be performed. For example, a higher weight is given to a gym than to a park.

Although the procedure 400 is described as detecting the various activity indicators sequentially in a particular order and determining the activity score after the activity indicators have each been detected, the activity score may be determined or adjusted in numerous ways. For example, as illustrated in FIG. 4, the activity score may be determined after detecting any one or more of the described activity indicators and their respective context in any combination. The precise order of the operations illustrated in FIG. 4 from 404-410 is shown for illustrative purposes. The operations performed from 404-410 may occur in any order, or in parallel. The activity score may be determined or calculated (e.g., updated) after each of the activity indicators have been detected, or after the selected group of indicators has been detected. Each activity indicator may be weighted similarly to any other activity indicator, or differently from any other activity indicator.

The activity score is compared to a threshold at 410. For example, the activity score is compared to the threshold, at 316, a predefined period of time after an initial activity indicator is received. If the activity score is less than the threshold at 410, the procedure 400 stops. If the activity score is greater than or equal to the threshold, management of the diabetic condition is performed at 412. For example, management of the diabetic condition includes autonomously controlling the basal rate of a user's insulin pump in response to the activity. Further, the insulin delivered via the pump is an appropriate value based on the strenuousness of the activity, the user, and the time of day, such that insulin is not wasted. The insulin levels may be dependent on the user and the user's activity. Lower or moderate levels of activity may result in a decrease in blood glucose level, therefore the insulin pump providing a standard or reduced basal rate would be appropriate. An increased amount of insulin is delivered by the body in response to higher or more strenuous levels of activity. For example, shorter term, higher intensity anaerobic activity stimulates the hormones that counteract the effects of insulin for a period of time (e.g., an hour or two) after the activity stops. For such activities, the body's basal rate may be elevated during the activity and for a period after the activity. The management of the diabetic condition also includes providing alerts to the user regarding blood glucose levels and insulin delivery in response to the activity.

The basal rate on the user's insulin pump may be adjusted automatically, or in response to a request presented to the user on the user device. For example, the insulin pump has different profiles that include different basal rates. The insulin pump has an "Exercise" profile on the insulin pump. In response to the activity score being at or above the predefined threshold, the user device automatically adjusts the basal rate to the "Exercise" profile to adjust the basal rate on the insulin pump or displays a request to the user to indicate whether to adjust the profile.

Figure 5A:
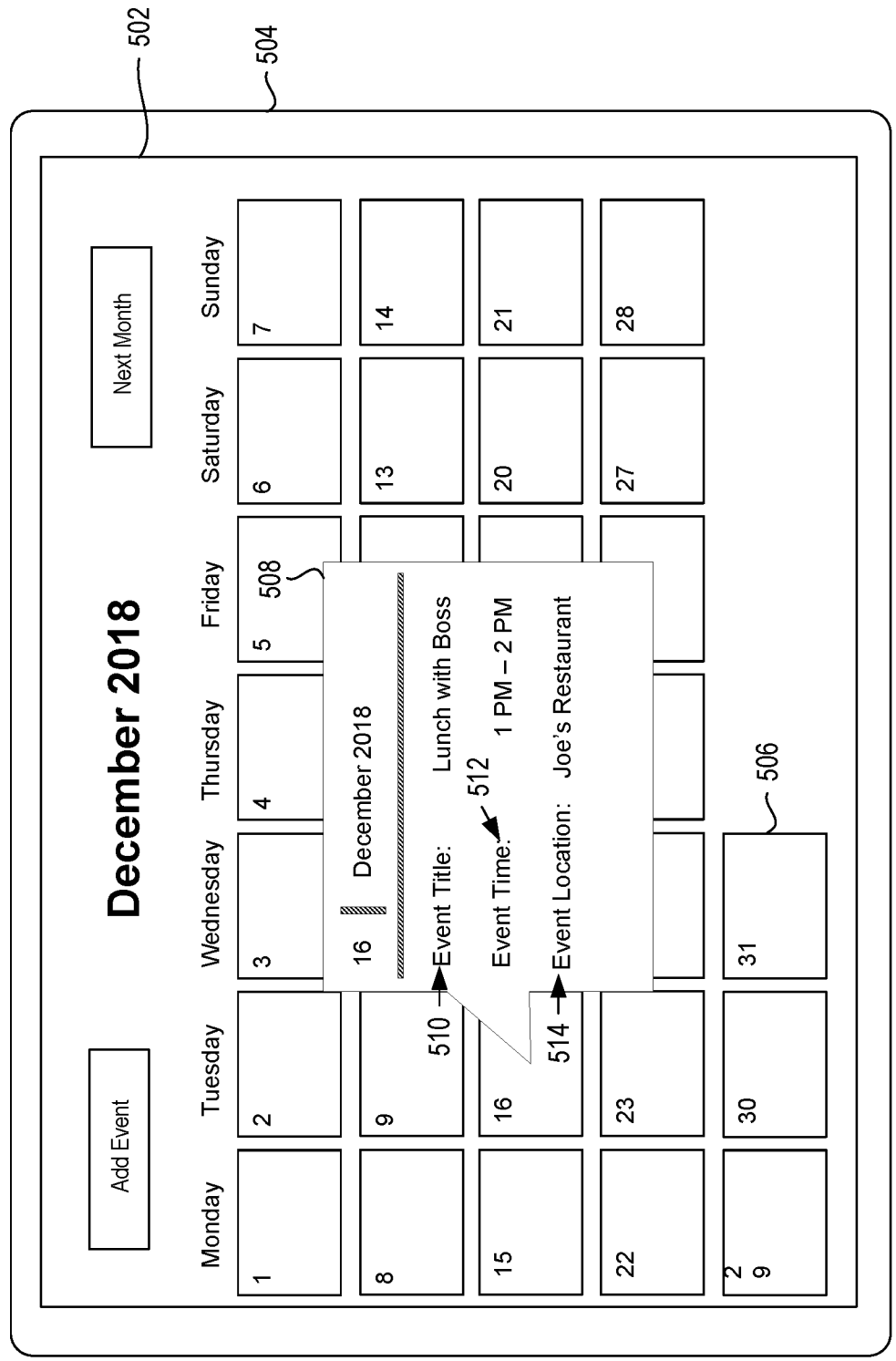
FIGS. 5A and 5B illustrate an example graphical user interface (GUI) that may display calendar information used to determine the location of a user.
Figure 5B:
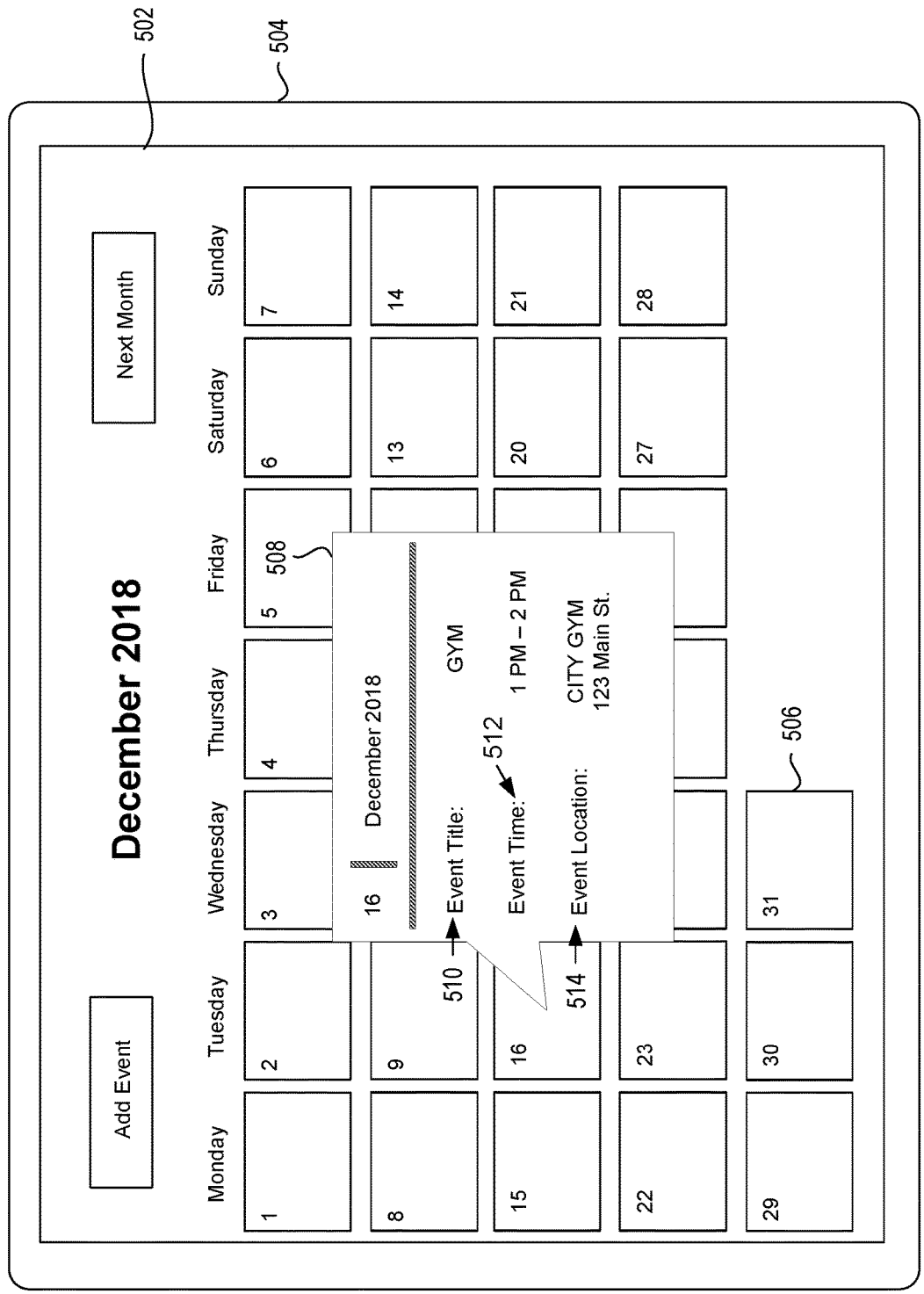

FIGS. 5A and 5B illustrate example graphical user interface (GUI) that display calendar information used to determine the location of a user. For example, the GUIs is displayed on user device 504. User device 504 is any user device with a display that is capable of accessing calendar information. For example, user device 504 is a smartphone, a wearable device, a laptop, a tablet, a BGM, a CGM controller, or any other device capable of displaying a GUI.

As shown in FIG. 5A, the GUI 502 displays a calendar 506. The calendar 506 is shown including hours, days, months. The GUI 502 displays a prescheduled event 508 that displays information about a specific calendar event. The information includes the event title 510, the event time 512, and the event location 514. The user device 504 uses the event time 512 to determine whether there is a current event or whether the event is occurring in a predefined period of time for triggering a keyword indicator. The user device 504 uses the event title 510 and the event location 514 to determine keywords for the event. The user device 504 matches the keywords to one or more keyword indicators for identifying a keyword indicator and calculating a mealtime score or an activity score. Keyword mining includes searching for a meal-related word or a meal-related location in the pre-scheduled event 508 to detect the keyword indicator.

As shown in FIG. 5A, the event title 510, the event time 512, and the event location 514 are mined for detecting a keyword indicator to determine that a user is consuming or is likely to consume a meal. The pre-scheduled event 508 includes one or more meal-related words (e.g., "Lunch," and "Restaurant") in the title 510 or the location 514, which triggers the keyword indicator to be detected. For example, pre-schedule event location 514 (e.g. Joe's Restaurant) may be cross referenced with a list of businesses and locations where a meal is likely to be consumed. If pre-schedule event location 514 (e.g. Joe's Restaurant) indicates that the user is at a location where a meal is likely to be consumed, the keyword indicator is detected.

FIG. 5B illustrates another example of the GUI 502 that comprises event information that is used to determine that a user is engaging or is likely to engage in elevated activity. As illustrated in FIG. 5B, the pre-scheduled event 508 includes an activity-related word (e.g., "Gym") in the title and location, which triggers the keyword indicator to be detected. For example, the location 514 of the pre-scheduled event 508 (e.g. City Gym or 123 Main Street) is cross referenced with a list of businesses and locations where a user is likely to engage in elevated activity (e.g., exercise). If location 514 of the pre-scheduled event 508 (e.g. City Gym and/or 123 Main Street) indicates a location where a user is likely to engage in elevated activity, the keyword indicator is detected.

Figure 6:
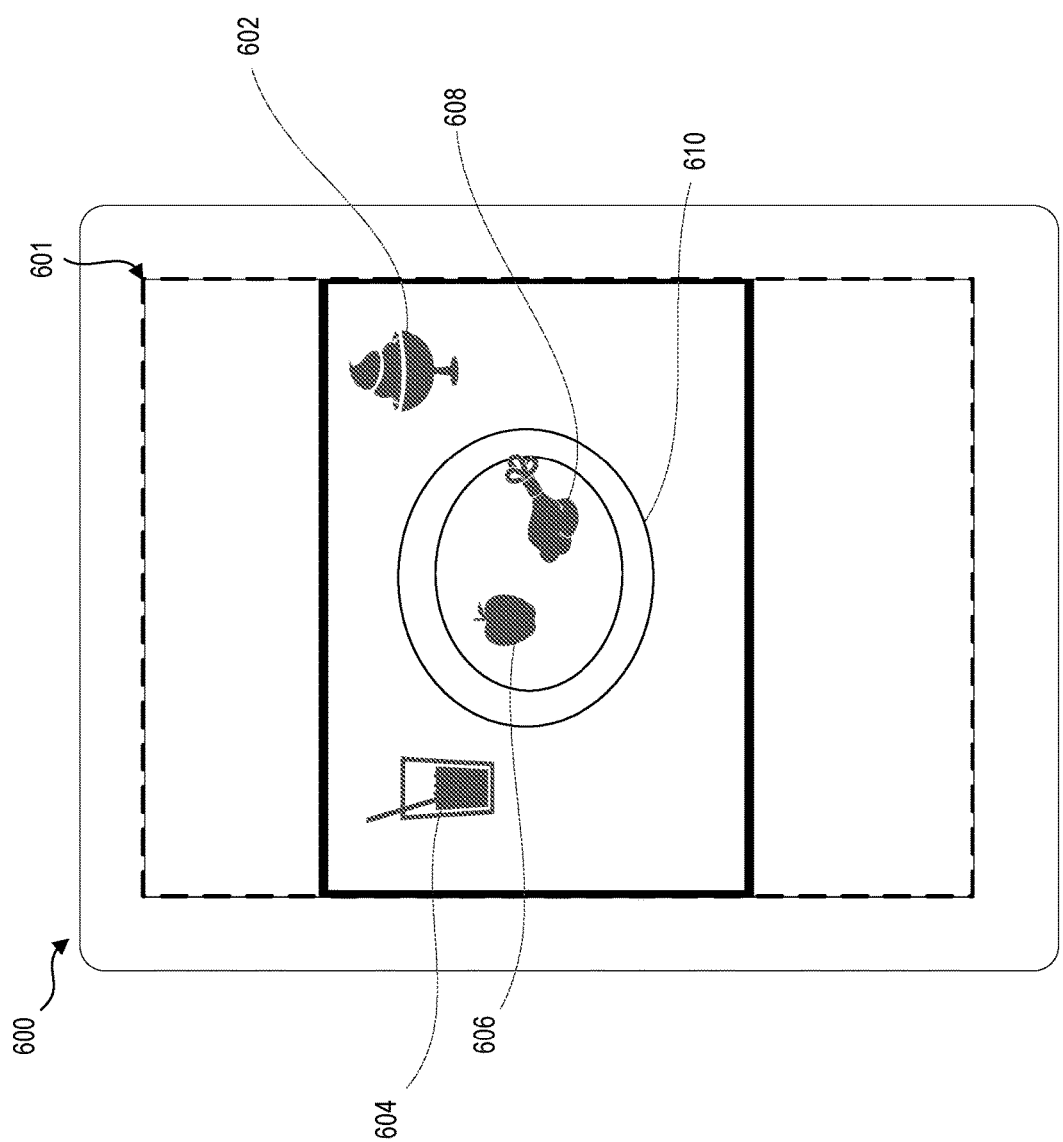
FIG. 6 illustrates a display of an example photograph that may be taken on a user device and may be used for detection of a photograph indicator.

FIG. 6 illustrates a display of an example photograph 601 that is taken on a user device 600 and is used for detection of a photograph indicator. As described herein, the photograph indicator is used to determine that a user is about to consume or is likely to consume a meal. As illustrated a in FIG. 6, a user captures the photograph 601 via a user device 600 (e.g., the mobile phone 104). The photograph 601 is processed to determine whether the photograph is a photograph of food or a meal-related item. As described herein the photograph indicator is detected when a user captures a photograph of food or another meal-related item.

Photograph processing to determine whether a user captured a photograph of food or a meal-related item includes detecting one or more items associated with food. For example, the items associated with food includes a plate, a bowl, a cup, or an item of food. Multiple items in the photograph 601 may be associated with food. For example, as illustrated in FIG. 6, the plate 610, the bowl 602, and the cup 604 are items associated with food. Similarly, the apple 606 and the poultry 608 within the photograph 601 are items of food. As more meal-related items are identified, the weight of the photograph indicator is increased. As the photograph 601 includes various items associated with food, the photograph 601 is determined to be a photograph of a meal-related item and the photograph indicator is detected.

The photograph 601 may be compared to one or more prestored images. The prestored images include examples of food photographs or other meal-related food items. The photograph 601 and the various items within the photograph 601 are compared to the prestored images to determine similarities between the items in the images. For example, the portion of the photograph 601 that includes the plate 610 is compared to prestored images to determine if the photograph 601 is a photograph of a meal-related item. If the similarity of the portions of the plate 610, or other portions of the photograph 601, is above a threshold, the photograph 601, or the analyzed portions thereof, are determined to be a photograph of a meal-related item. The triggering event for performing analysis of the photograph 601 may be the action of taking the photograph, or when the photograph 601 is uploaded to an application.

Figure 7A:
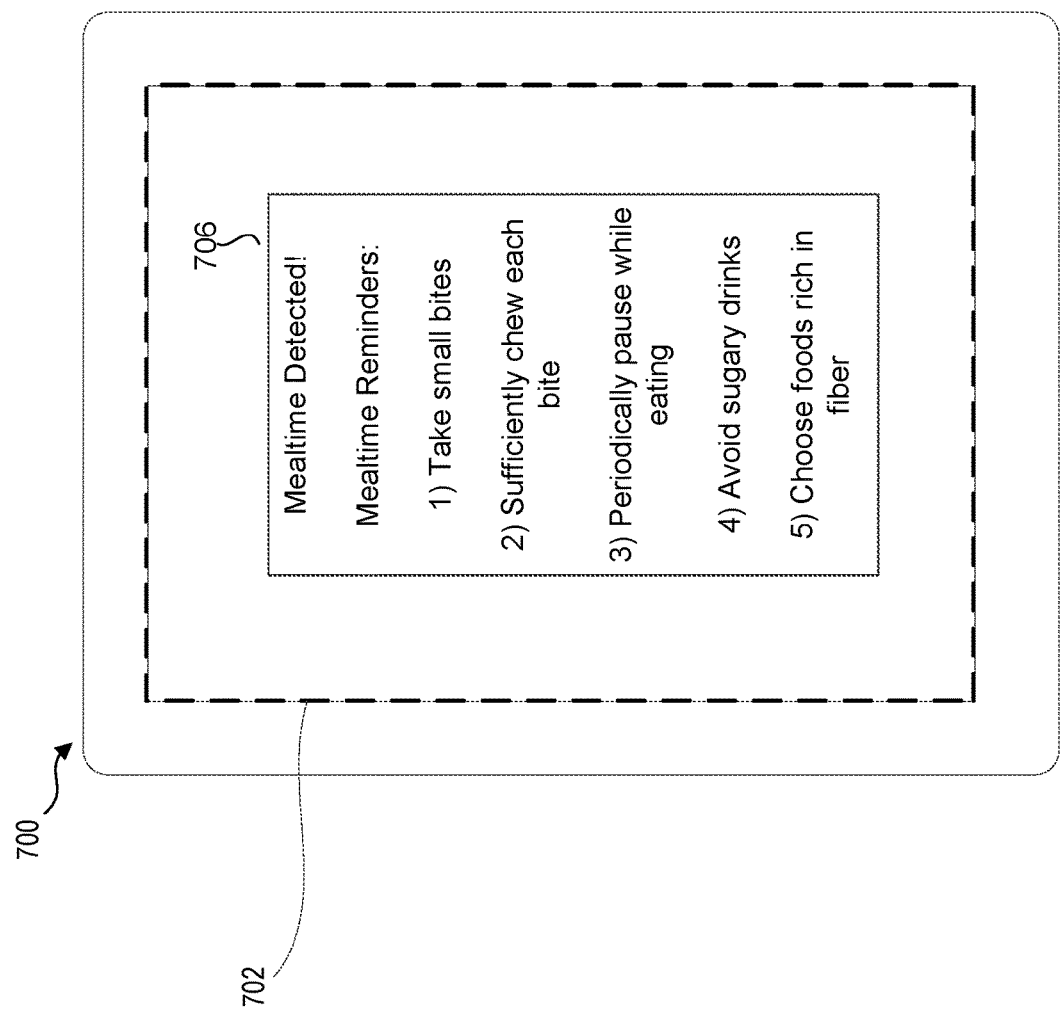
FIGS. 7A and 7B illustrate example GUIs that include mealtime alerts that may be provided to a user.
Figure 7B:
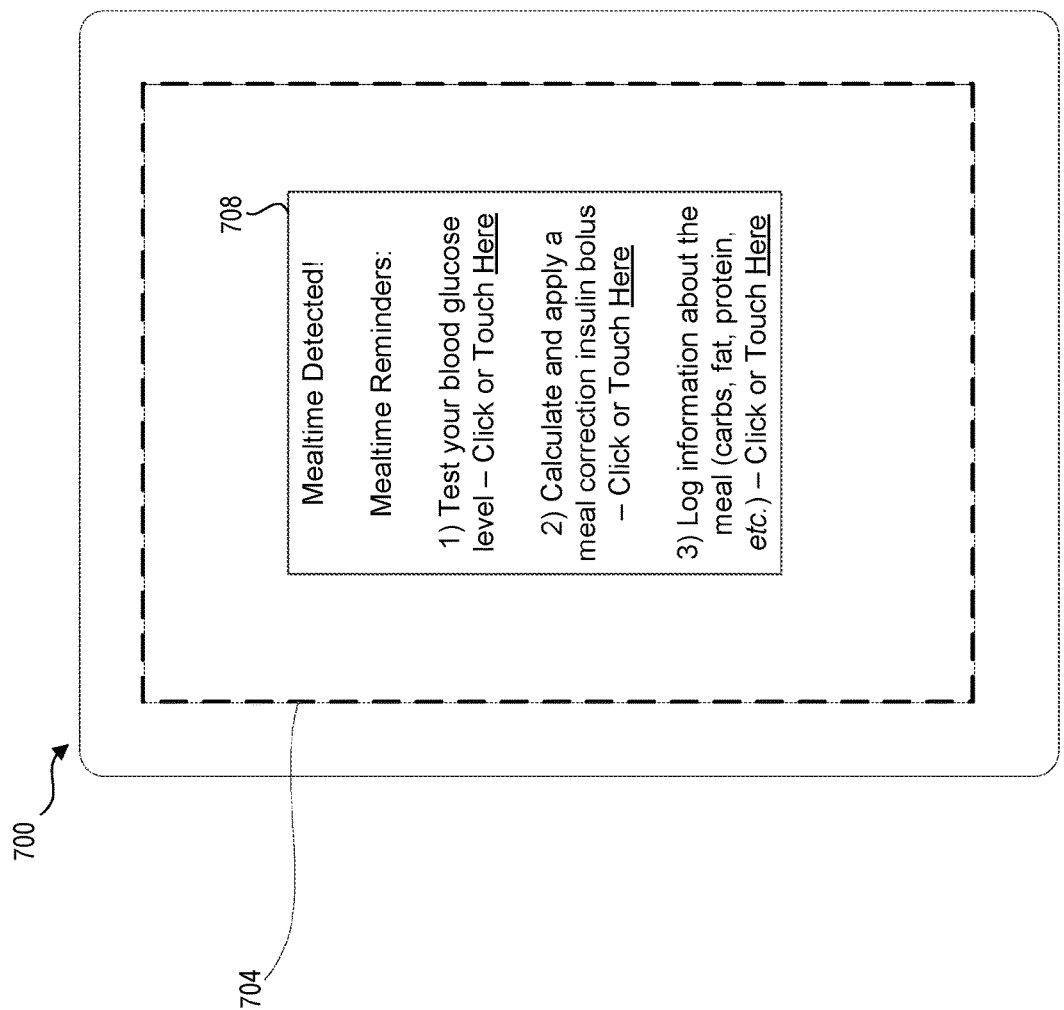

FIGS. 7A and 7B illustrate example GUIs 702, 704 that include mealtime alerts 706, 708 that are provided on a user device 700. As illustrated in FIGS. 7A and 7B, mealtime alerts 706, 708 are provided via a user device 700. The mealtime alerts 706, 708 are provided via respective GUIs 702, 704 that are generated locally at the user device 700, or at a remote computing device and displayed via a local application (e.g., web browser).

As described herein, the mealtime alerts 706, 708 are a form of management of the diabetic condition and include a reminder for the user to perform another form of management of the diabetic condition. Further, the mealtime alerts 706, 708 are provided to a user proximate to when the user is about to consume a meal, for example, based on the detection of one or more mealtime indicators.

The manner in which the mealtime alerts 706, 708 are provided to the user depends on the mealtime indicators detected and the mealtime score. Similarly, the form of management of the diabetic condition that the mealtime alerts 706, 708 indicate that the user should perform depends on the mealtime indicators detected and the mealtime score.

The mealtime alerts 706, 708 may be provided to the user before and/or after the user consumes a meal. FIG. 7A illustrates an example where the mealtime alert 706 is provided to user before the user consumes a meal. FIG. 7B illustrates an example where the mealtime alert 708 is provided to the user after the user consume a meal.

As illustrated in FIG. 7A, a mealtime alert 706 is provided to a user before the user consumes a meal. The mealtime alert 706 includes a reminder to perform management of the diabetic condition by providing the user with suggestion to aid the user in reducing their BMI. For example, as illustrated in FIG. 7A, the mealtime alert 706 includes an indication to take smaller bites, sufficiently chew each bite, periodically pause while eating, avoid sugary drinks, and choose food rich in fiber. The mealtime alert 706 is provided to the user proximate to the user consuming a meal, such that the user does not forget to perform management of the diabetic condition while consuming the meal. The mealtime alert 706 is provided to user via a user device commonly used by the user (e.g., the mobile phone 104), which increases the likelihood that the user receives and reads the mealtime alert 706. Accordingly, the mealtime alert 706 increases the likelihood that the user performs management of the diabetic condition.

Although FIG. 7A illustrates certain types of reminder included in the mealtime alert 706, other reminders may also be included in a mealtime alert. Further, the reminders included in the mealtime alert 706 may be based on the contextual relevance of the detected mealtime indicators. For example, if the location indicator is detected, a reminder that assists the user in ordering food at that location (e.g., based on a menu available for the location) is included in the mealtime alert. The reminder includes certain criteria for assisting the user in ordering food at the location (e.g., low-calorie foods, high-fat foods, or low-carb foods). The mealtime alert 706 or other reminders being provided when the user approaches a location may assist in providing reminders at a time that is likely prior to the user selecting a meal. The mealtime alert 706 includes a reminder of an amount of calories that have been consumed for the day, a reminder of the user's current blood glucose level, and a suggested amount of carbs to consume (e.g., a number not to be exceeded in a period of time to prevent an extreme diabetic condition).

Detecting a meal might prompt the system to show the user her current BG level and suggest an appropriate amount of carbs to consume, for example, to exit a hypo state or to not consume so much as to far exceed the after-meal target BG range.

Referring now to FIG. 7B, a mealtime alert 708 is provided to a user after the user consumes a meal. The mealtime alert 708 includes a reminder to perform management of the diabetic condition. For example, as illustrated in FIG. 7B, the mealtime alert 708 includes an indication for the user to: test their blood glucose level, calculate and apply a meal correction insulin bolus, and log information about the meal consumed by the user. The mealtime alert 708 is provided to the user proximate to the user consuming a meal, such that the user may not forget to perform management of the diabetic condition. Similarly, the mealtime alert 708 is provided to user via a user device commonly used by the user (e.g., the mobile phone 104), which increases the likelihood that the user receives and reads the mealtime alert 708. Accordingly, the mealtime alert 708 increases the likelihood that the user performs management of the diabetic condition. The mealtime alert 708 includes links for the user to easily and quickly perform the indicated form of management of the diabetic condition. Accordingly, the mealtime alert 708 increases the likelihood that the user performs management of the diabetic condition in a timely manner.

Figure 8:
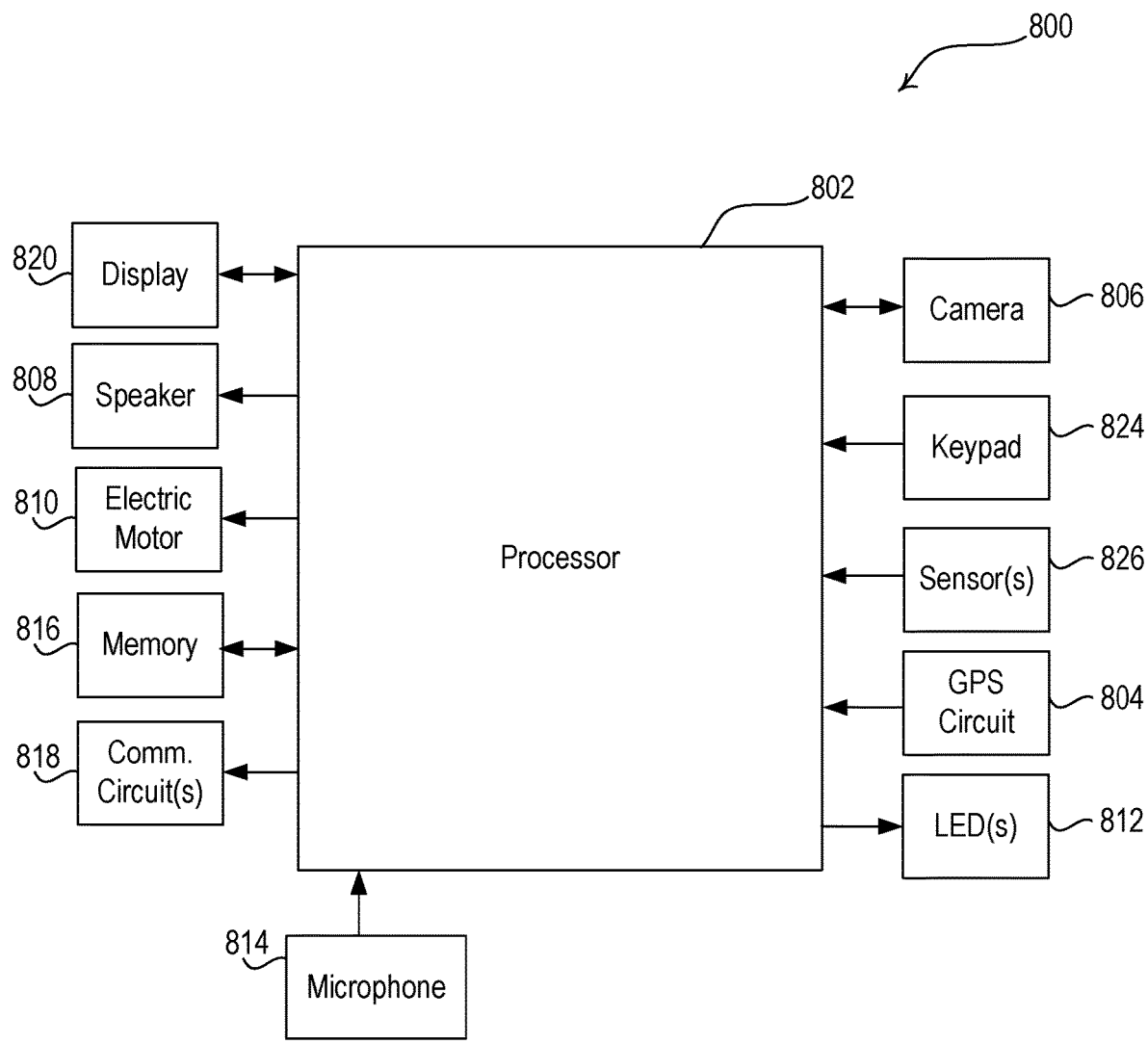
FIG. 8 is a block diagram of an example computing device.

FIG. 8 is a block diagram of an example computing device 800. The computing device is a mobile computing device, such as a tablet, a cellular phone, a wearable device, a CGM controller device, or another computing device, for example. As shown in FIG. 8, the computing device 800 includes a processor 802 for controlling the functionality of the computing device 800. The processor 802 includes one or more circuits, such as general-purpose processors, special purpose processors, conventional processors, digital signal processors (DSPs), microprocessors, integrated circuits, a programmable logic device (PLD), application specific integrated circuits (ASICs), or the like. The processor 802 performs signal coding, data processing, power control, image processing, input/output processing, or any other functionality that enables the computing device 800 to perform as described herein.

The processor 802 stores information in or retrieve information from the memory 816. The memory 816 includes a non-removable memory or a removable memory. The non-removable memory includes random-access memory (RAM), read-only memory (ROM), a hard disk, or any other type of non-removable memory storage. The removable memory includes a subscriber identity module (SIM) card, a memory stick, a memory card (e.g., a digital camera memory card), or any other type of removable memory. The processor 802 accesses the memory 816 for executable instructions or other information that is used by the computing device 800.

The computing device 800 includes a camera 806 that is in communication with the processor 802. The camera 806 is a digital camera or other optical device capable of generating images or videos (e.g., image sequences) for being captured at the computing device 800. The camera 806 includes a lighting device capable of flashing to in response to signals from the processor 802. The lighting device flashes to provide alerts via the camera 806.

The computing device 800 includes one or more communication circuits 818. The processor 802 is in electrical communication with the communication circuit 818 for sending or receiving information. The communication circuit 818 is capable of performing wired or wireless communications. For example, the communication circuit 818 includes one or more radio frequency (RF) transceivers for transmitting and receiving RF signals (e.g., BLUETOOTH®, near field communication (NFC), WIFI®, WI-MAX®, cellular, or other RF signals) via an antenna, or other communications module capable of performing wireless communications. In some embodiments, one or more communication circuits 818 are capable of performing infrared (IR) communications.

The processor 802 is in electrical communication with a keypad 824 for providing input to the processor 802. The keypad 824 includes one or more keys for receiving input from a user. The keypad 824 includes hard or soft keys for which the function of the keys changes as a user performs selections.

Other input into the processor 802 is provided by one or more sensors 826. The sensors 826 include a motion sensor, a proximity sensor, a heartrate monitoring sensor, an accelerometer, a gyroscope, or another sensor on the computing device. The motion sensor transmits infrared signals or uses image processing to sense movement. The proximity sensor transmits infrared signals to detect when an object is within a predefined proximity. The heartrate monitoring sensor implements photoplethysmography to detect the amount of blood flow in the user. The heartrate monitoring sensor includes one or more LED or photodiodes to detect the amount of blood flow in the user. The heartrate monitoring sensor implements infrared technology to detect the amount of blood flow in the user. The heartrate monitoring sensor takes an electrocardiogram (ECG) and detects information about the user's heartrate from the ECG. The accelerometer measures the non-gravitational acceleration of the computing device 800 in a given direction. The accelerometer responds to vibrations associated with movement in a given direction. The measurements from the accelerometer are used by the processor 802 to determine the magnitude or direction of the relative movement of the computing device 800, or the user's relative position (e.g., standing, sitting, or lying down). The gyroscope is used to determine the orientation of the computing device 800.

The processor 802 is in electrical communication with or generate images on a display 820 for providing information to a user. The communication between the display 820 and the processor 802 is a two-way communication, as the display 820 includes a touch screen module capable of receiving information from a user and providing such information to the processor 802. For example, the display 820 provides soft buttons for selection by a user that are recognized by the touch screen module and provided to the processor 802 as input.

The processor 802 is in electrical communication with or control a speaker 808. The speaker 808 provides an audible sound (e.g., tone, beep, or buzz) in response to a triggering event detected by the processor 802.

The computing device 800 includes an electric motor 810 that is in electrical communication with or controlled by the processor 802. The electric motor 810 rotates and causes the computing device 800 to vibrate (e.g., to indicate an alert) in response to a triggering event detected by the processor 802. The electric motor 810 provides an alert to supplement the audible alarm or replace the audible alarm provided by the speaker 808.

The processor 802 is in electrical communication with or receive information from a microphone 814. For example, the processor 802 receives audio signals via the microphone 814.

The computing device 800 includes a global positioning system (GPS) circuit 804. The GPS circuit 804 is capable of receiving GPS information. The processor 802 is capable of determining the GPS coordinates (e.g., latitude and longitude) of the computing device 800 based on the GPS information received via the GPS circuit.

The computing device 800 includes a visual indicator, such as one or more light-emitting diodes (LEDs) 812. In some embodiments, one or more LEDs 812 are illuminated or flashed to provide an alert or communicate other information to the user (e.g., low battery or turning on of the device)

Figure 9:
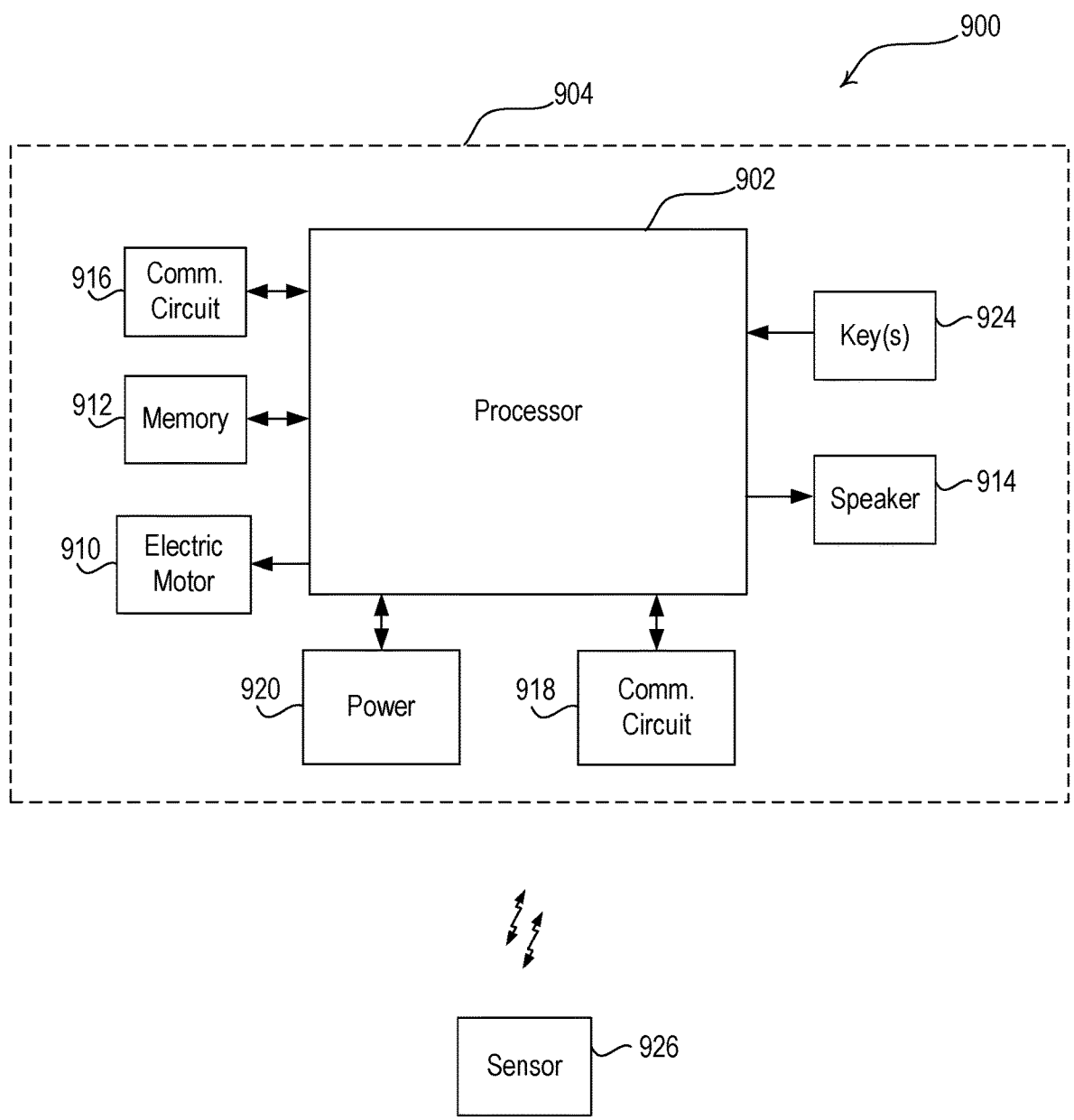
FIG. 9 is a block diagram of an example blood glucose monitoring device.

FIG. 9 is a block diagram of an example blood glucose monitoring device 900. In some embodiments, the blood glucose monitoring device 900 is a CGM or FGM, for example. The blood glucose monitoring device 900 includes a subcutaneous sensor 926 that is used to sense and monitor the amount of glucose in interstitial fluid of the user. Data is transmitted from the sensor 926 to a transmitting device 904. When the blood glucose monitoring device 900 is a CGM, the transmitting device 904 is located directly over the sensor 926 and wirelessly powers the data transfer from the sensor 926 via power supply 920. When the blood glucose monitoring device 900 is an FGM, the transmitting device 904 is a mobile device or other reader device that instantaneously receives the blood glucose information from the sensor 926 when the device is within the RF range of the sensor 926.

The transmitting device 904 receives data communications from the sensor 926 via a communication circuit 918. The communication circuit 918 is in electrical communication with a processor 902. The processor 902 includes one or more circuits, such as general-purpose processors, special purpose processors, conventional processors, digital signal processors (DSPs), microprocessors, integrated circuits, a programmable logic device (PLD), application specific integrated circuits (ASICs), or the like. The processor 902 performs signal coding, data processing, power control, input/output processing, or any other functionality that enables the transmitting device 904 to perform as described herein.

The transmitting device 904 includes another communication circuit 916 for communicating with other devices. The processor 902 is in electrical communication with the communication circuit 916 for sending or receiving information. The communication circuits 916, 918 are capable of performing wired or wireless communications. For example, the communication circuits 916, 918 include one or more radio frequency (RF) transceivers for transmitting and receiving RF signals (e.g., BLUETOOTH®, near field communication (NFC), WIFI®, WI-MAX®, cellular, or other RF signals) via an antenna, or other communications module capable of performing wireless communications. The communication circuits 916, 918 communicate using the same RF protocol or a different RF protocol.

The processor 902 stores information in or retrieves information from the memory 912. The memory 912 includes a non-removable memory or a removable memory. The non-removable memory includes random-access memory (RAM), read-only memory (ROM), a hard disk, or any other type of non-removable memory storage. The removable memory includes a subscriber identity module (SIM) card, a memory stick, a memory card (e.g., a digital camera memory card), or any other type of removable memory. The processor 902 accesses the memory 912 for executable instructions or other information that is used by the transmitting device 904. The processor 902 is in electrical communication with a one or more input keys 924 for providing input to the processor 902.

The processor 902 is in electrical communication with or control a speaker 914. The speaker 914 provides an audible sound (e.g., tone, beep, or buzz) in response to a triggering event detected by the processor 902.

The blood glucose monitoring device 900 includes an electric motor 910 that is in electrical communication with or controlled by the processor 902. The electric motor 910 rotates and causes the blood glucose monitoring device 900 to vibrate (e.g., to indicate an alert) in response to a triggering event detected by the processor 902. The electric motor 910 provides an alert to supplement the audible alarm or replace the audible alarm provided by the speaker 914.

Figure 10:
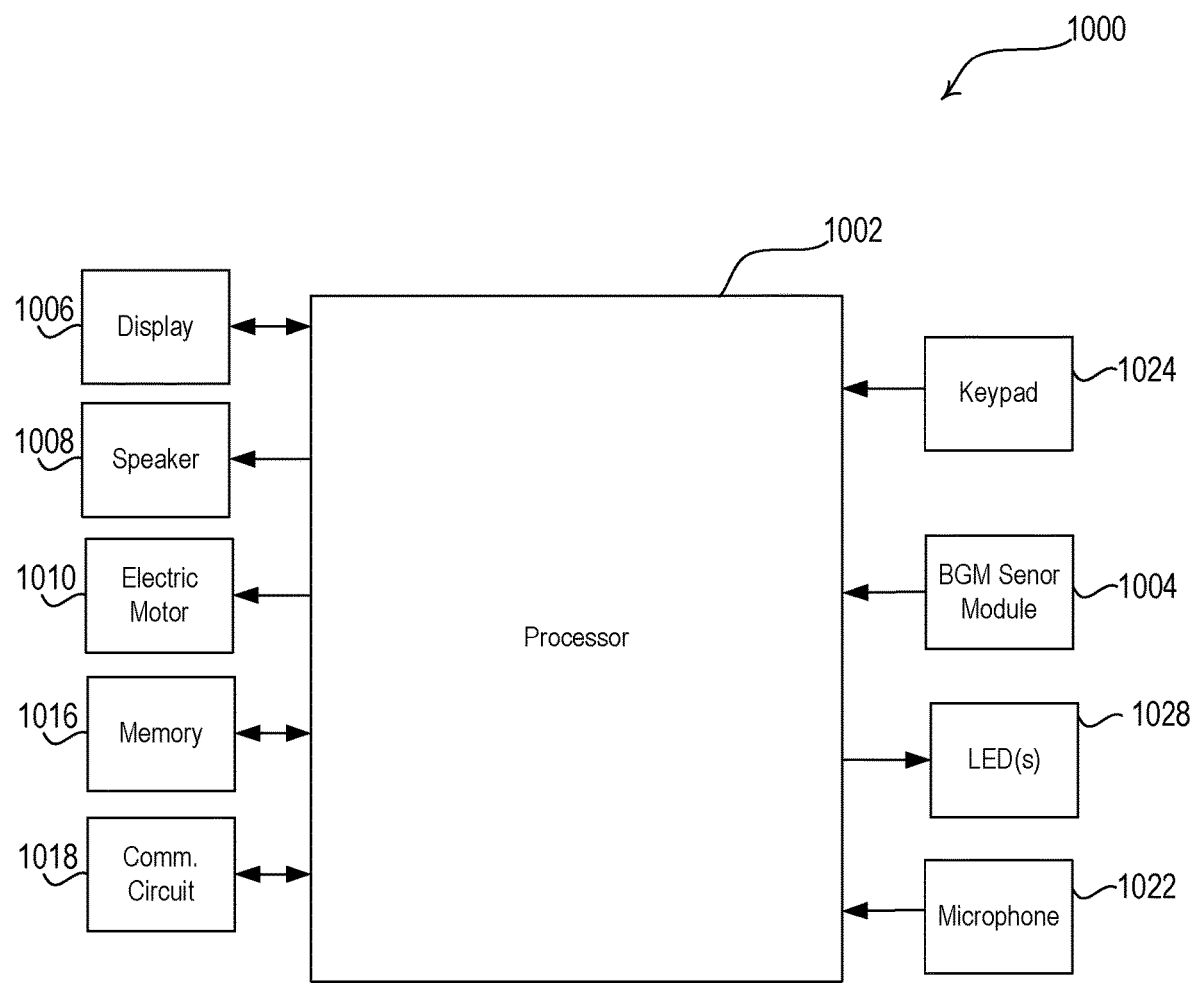
FIG. 10 is a block diagram of an example blood glucose measuring (BGM) device.

FIG. 10 is a block diagram of an example blood glucose measuring (BGM) device 1000. As shown in FIG. 10, the BGM device 1000 includes a processor 1002 for controlling the functionality of the BGM device 1000. The processor 1002 includes one or more circuits, such as general-purpose processors, special purpose processors, conventional processors, digital signal processors (DSPs), microprocessors, integrated circuits, a programmable logic device (PLD), application specific integrated circuits (ASICs), or the like. The processor 1002 performs signal coding, data processing, power control, image processing, input/output processing, or any other functionality that enables the BGM device 1000 to perform as described herein.

The processor 1002 stores information in or retrieve information from the memory 1016. The memory 1016 includes a non-removable memory or a removable memory. The non-removable memory includes random-access memory (RAM), read-only memory (ROM), a hard disk, or any other type of non-removable memory storage. The removable memory includes a subscriber identity module (SIM) card, a memory stick, a memory card (e.g., a digital camera memory card), or any other type of removable memory. The processor 1002 accesses the memory 1016 for executable instructions or other information that is used by the BGM device 1000.

The BGM device 1000 includes one or more communication circuits 1018. The processor 1002 is in electrical communication with the communication circuit 1018 for sending or receiving information. The communication circuit 1018 is capable of performing wired or wireless communications. For example, the communication circuit 1018 includes one or more radio frequency (RF) transceivers for transmitting and receiving RF signals (e.g., BLUETOOTH®, near field communication (NFC), WIFI®, WI-MAX®, cellular, or other RF signals) via an antenna, or other communications module capable of performing wireless communications. In some embodiments, one or more communication circuits 1018 are capable of performing infrared (IR) communications.

The processor 1002 is in electrical communication with a keypad 1024 for providing input to the processor 1002. The keypad 1024 includes one or more keys for receiving input from a user. The keypad 1024 includes hard or soft keys for which the function of the keys changes as a user performs selections.

Other input into the processor 1002 is provided by the BGM sensor module 1004. The BGM sensor module 1004 includes a blood glucose measuring engine that may analyze blood samples provided by a patient on a blood glucose measurement strip and measures the amount of blood glucose in the samples.

The processor 1002 is in electrical communication with or generate images on a display 1006 for providing information to a user. The communication between the display 1006 and the processor 1002 is a two-way communication, as the display 1006 includes a touch screen module capable of receiving information from a user and providing such information to the processor 1002. For example, the display 1006 provides soft buttons for selection by a user that are recognized by the touch screen module and provided to the processor 1002 as input.

The processor 1002 is in electrical communication with or control a speaker 1008. The speaker 1008 provides an audible sound (e.g., tone, beep, or buzz) in response to a triggering event detected by the processor 1002.

The BGM device 1000 include an electric motor 1010 that is in electrical communication with or controlled by the processor 1002. The electric motor 1010 rotates and causes the BGM device 1000 to vibrate (e.g., to indicate an alert) in response to a triggering event detected by the processor 1002. The electric motor 1010 provides an alert to supplement the audible alarm or replace the audible alarm provided by the speaker 1008.

The processor 1002 is in electrical communication with or receive information from a microphone 1022. For example, the processor 1002 receives audio signals via the microphone 1022.

The BGM device 1000 includes a visual indicator, such as one or more one or more light-emitting diodes (LEDs) 1028. In some embodiments, one or more LEDs 1028 are illuminated or flashed to provide an alert or communicate other information to the user (e.g., low battery or turning on of the device).

Figure 11:
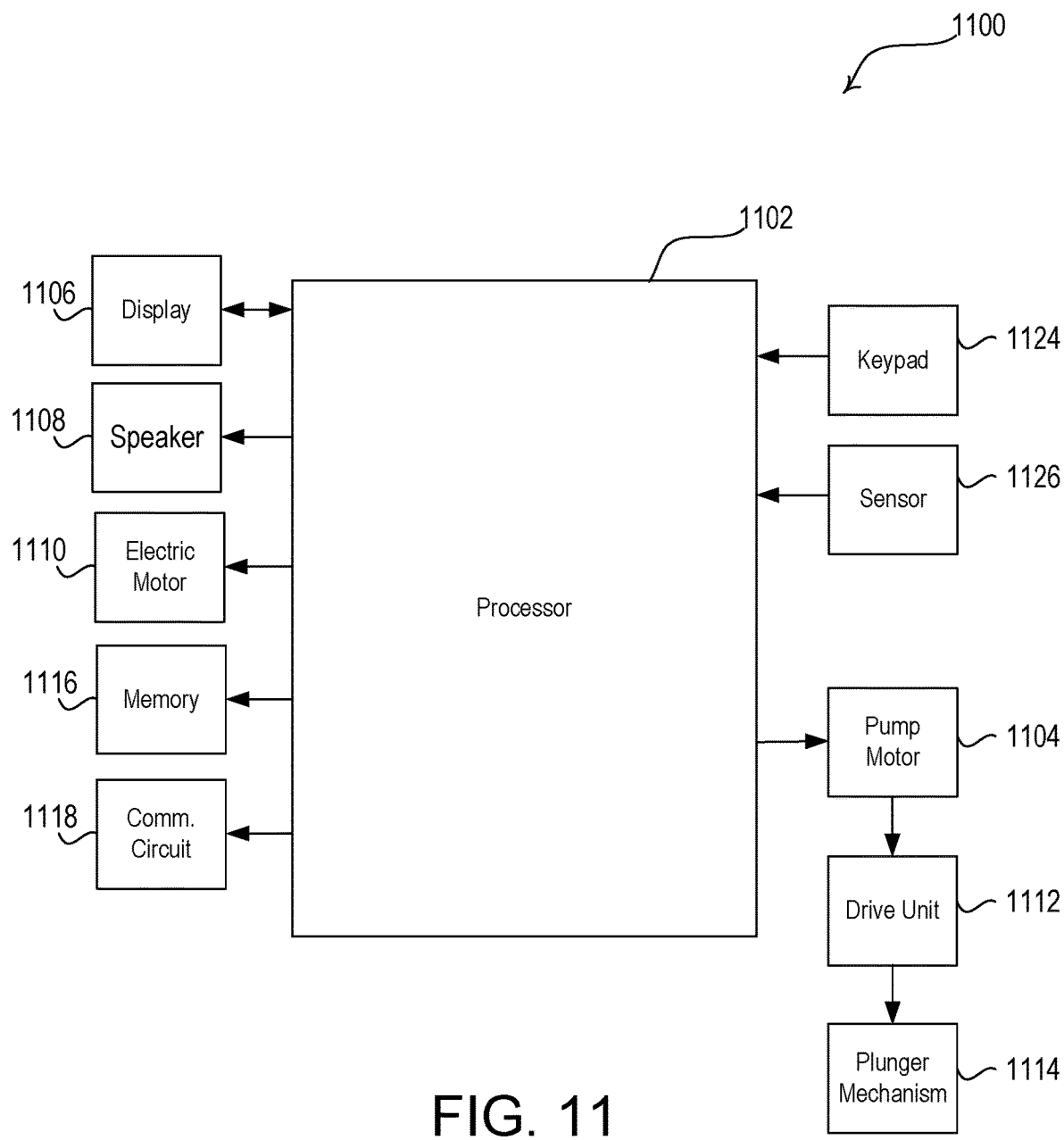
FIG. 11 is a block diagram illustrating an example of an insulin pump.

FIG. 11 is a block diagram illustrating an example of an insulin pump 1100. As shown in FIG. 11, the insulin pump 1100 includes a processor 1102. The processor 1102 includes one or more circuits, such as general-purpose processors, special purpose processors, conventional processors, digital signal processors (DSPs), microprocessors, integrated circuits, a programmable logic device (PLD), application specific integrated circuits (ASICs), or the like. The processor 1102 performs signal coding, data processing, power control, image processing, input/output processing, or any other functionality that enables the insulin pump 1100 to perform as described herein.

The processor 1102 is in electrical communication with or control a pump motor 1104 in the insulin pump 1100. The pump motor 1104 drives a drive unit 1112 that pushes a plunger mechanism 1114. The plunger mechanism 1114 ejects insulin from an insulin cartridge (not shown). The insulin cartridge includes a supply of insulin for delivery to a user.

The processor 1102 is in electrical communication with or generate images on a display 1106 for providing information to a user. The communication between the display 1106 and the processor 1102 is a two-way communication, as the display 1106 includes a touch screen module capable of receiving information from a user and providing such information to the processor 1102. For example, the display 1106 provides soft buttons for selection by a user that are recognized by the touch screen module and provided to the processor 1102 as input.

The processor 1102 is in electrical communication with or control a speaker 1108. The speaker 1108 provides an audible sound (e.g., tone, beep, or buzz) in response to a triggering event detected by the processor 1102.

The insulin pump 1100 includes an electric motor 1110 that is in electrical communication with or controlled by the processor 1102. The electric motor 1110 rotates and causes the insulin pump to vibrate (e.g., to indicate an alert) in response to a triggering event detected by the processor 1102. The electric motor 1110 provides an alert to supplement the audible alarm or replace the audible alarm provided by the speaker 1108.

The processor 1102 is in electrical communication with a memory 1116. The processor stores information in or retrieve information from the memory 1116. The memory 1116 includes a non-removable memory or a removable memory for storing computer-readable media. The non-removable memory includes random-access memory (RAM), read-only memory (ROM), a hard disk, or any other type of non-removable memory storage. The removable memory includes a subscriber identity module (SIM) card, a memory stick, a memory card (e.g., a digital camera memory card), or any other type of removable memory. The processor 1102 accesses the memory 1116 for executable instructions or other information that is used by the insulin pump 1100.

The insulin pump 1100 includes a communication circuit 1118. The processor 1102 is in electrical communication with the communication circuit 1118 for sending or receiving information. The communication circuit 1118 is capable of performing wired or wireless communications. For example, the wireless communications circuit 1118 includes a radio frequency (RF) transceiver for transmitting and receiving RF signals (e.g., BLUETOOTH®, near field communication (NFC), WIFI®, WI-MAX®, cellular, or other RF signals) via an antenna, or other communications module capable of performing wireless communications. In some embodiments, the communication circuit 1118 is capable of performing infrared (IR) communications.

The processor 1102 is in electrical communication with a keypad 1124 for providing input to the processor 1102. The keypad 1124 includes one or more keys for receiving input from a user. The keypad 1124 includes hard or soft keys for which the function of the keys changes as a user performs selections.

Other input into the processor 1102 is provided by sensors 1126. The sensor 1126 includes a pressure sensor that is sensitive to the pressure within a reservoir of insulin; a cartridge sensor that is sensitive to the presence of an insulin cartridge or a motion sensor that detects the motion of a gear (not shown) in the drive unit 1112.

Although features, elements, and functions are described above in particular combinations, a feature, element, or function is used alone or in any combination with the other features, elements, or functions. Various presently unforeseen or unanticipated alternatives, modifications, variations, or improvements may be subsequently made that are also intended to be encompassed by the following claims.

The methods described herein are implemented in a computer program, software, or firmware incorporated in a computer-readable medium for execution by a computer or processor. Examples of computer-readable media include electronic signals (transmitted over wired or wireless connections) and computer-readable storage media. Examples of computer-readable storage media include, but are not limited to, a read only memory (ROM), a random-access memory (RAM), removable disks, and optical media such as CD-ROM disks, and digital versatile disks (DVDs).

What is claimed is:

1. A method performed by a device comprising a battery and at least one processing circuit, the method comprising:
    detecting, via the at least one processing circuit on the device, a first mealtime indicator as a triggering event for determining a mealtime score for a user, wherein the first mealtime indicator is set at an estimated mealtime associated with the user;
    after detecting the first mealtime indicator, processing information associated with each of a plurality of second mealtime detection indicators in parallel to generate a respective value for each of the plurality of second mealtime detection indicators associated with the user, wherein the plurality of second mealtime detection indicators comprise:
    a blood glucose indicator that indicates a blood glucose level of the user; and
    at least one of:
        a photograph indicator that is based on a photograph of a meal-related item;
        a position indicator that indicates the user is in a position of the user;
        a location indicator that indicates a location of the device associated with the user; or
        a keyword indicator that indicates a keyword of a pre-scheduled event;
    determining, via the at least one processing circuit on the device, the mealtime score based on the respective value of each of the plurality of second mealtime detection indicators associated with the user;
    determining, via the at least one processing circuit on the device, that the mealtime score is below a mealtime threshold based on the respective value associated with each of the second mealtime detection indicators; and
    preventing, via the at least one processing circuit on the device, at least one mealtime alert from being displayed via a display of the device based on the mealtime score being below the mealtime threshold, wherein the at least one processing circuit on the device is configured to prevent the at least one mealtime alert from being provided via the display to save a power of the battery based on the estimated mealtime associated with the user failing to indicate a mealtime.

2. The method of claim 1, wherein the estimated mealtime is initially set to a first estimated mealtime, the method further comprising updating the estimated mealtime at which the first mealtime indicator is set from the first estimated mealtime to a second estimated mealtime based on a detection that a meal has been eaten or is likely to be eaten by the user at a time outside of the first estimated mealtime.

3. The method of claim 2, wherein the estimated mealtime is updated from the first estimated mealtime to the second estimated mealtime in response to the mealtime score being above a predefined threshold at the time outside of the first estimated mealtime.

4. The method of claim 2, wherein the estimated mealtime is updated from the first estimated mealtime to the second estimated mealtime in response to a number of mealtimes that are tracked over a period of time being detected as being outside of the first estimated mealtime.

5. The method of claim 1, further comprising:
controlling a basal rate of an insulin pump after detection of the mealtime based on the mealtime score.

6. The method of claim 1, wherein a weight value of the photograph indicator that is used for determining the mealtime score is different based on a confidence level that the photograph includes the meal-related item.

7. The method of claim 6, further comprising performing image processing of the photograph using a photo service that includes a neural network image classifier capable of identifying various types of meal-related items that have been learned from prestored images, and wherein the meal-related items are identified based on at least one of textures, patterns, spatial density, or shapes of items in the photograph.

8. The method of claim 1, wherein the mealtime score is determined based on the keyword indicator, and wherein a weight value of the keyword indicator that is used for determining the mealtime score is different based on the keyword or a number of keywords detected.

9. The method of claim 1, wherein the position indicator indicates the user is in a sitting position, and wherein the position indicator is based on information from a gyroscope or an accelerometer of the device associated with the user.

10. The method of claim 1, wherein the respective value of each of the second plurality of mealtime detection indicators comprises a respective weight value.

11. The method of claim 1, wherein the keyword comprises at least one of a meal-related word or a meal-related location mined from a title of the pre-scheduled event, and wherein a weight value of the keyword indicator that is used for determining the mealtime score is different based on the keyword or a number of keywords detected.

12. The method of claim 1, further comprising:
detecting, prior to determining the mealtime score, that a current time is at least a predefined period of time since a last mealtime associated with the user.

13. The method of claim 1, wherein the device comprises a glucose meter.

14. The method of claim 1, wherein the mealtime score comprises a first mealtime score, wherein the information comprises first information, wherein the respective value comprises a first respective vale, the method further comprising:
processing, via the at least one circuit on the device, second information associated with each of the plurality of second mealtime detection indicators in parallel to generate a second respective value for each of the plurality of second mealtime indicators associated with the user;
determining, via the at least one circuit on the device, a second mealtime score based on the second respective value of each of the plurality of second mealtime detection indicators associated with the user;
determining, via the at least one circuit on the device, that the second mealtime score is above the mealtime threshold based on the second respective value associated with each of the second mealtime detection indicators; and
providing the at least one mealtime alert to the user via the display to assist in treatment of a diabetic condition in response to the second mealtime score being above the mealtime threshold.

15. A device comprising:
a battery:
a display; and
at least one processor configured to:
detect a first mealtime indicator as a triggering event for determining a mealtime score for a user, wherein the first mealtime indicator is set at an estimated mealtime associated with the user;
after detecting the first mealtime indicator, process information associated with each of a plurality of second mealtime detection indicators in parallel to generate a respective value for each of the plurality of second mealtime detection indicators associated with the user, wherein the plurality of second mealtime detection indicators comprise:
a blood glucose indicator that indicates a blood glucose level of the user; and
at least one of:
a photograph indicator that is based on a photograph of a meal-related item;
a position indicator that indicates the user is in a position of the user;
a location indicator that indicates a location associated with the user; or
a keyword indicator that indicates a keyword of a pre-scheduled event;
determine the mealtime score based on the respective value of each of the plurality of second mealtime detection indicators associated with the user;
determine that the mealtime score is below a mealtime threshold based on the respective value associated with each of the second mealtime detection indicators; and
prevent at least one mealtime alert from being provided to the user via the display based on the mealtime score being below the mealtime threshold, wherein the at least one processor is configured to prevent the at least one mealtime alert from being provided via the display to save a power of the battery based on the estimated mealtime associated with the user failing to indicate a mealtime.

16. The device of claim 15, wherein the at least one processor is further configured to initially set the estimated mealtime to a first estimated mealtime, and wherein the at least one processor is further configured to update the estimated mealtime at which the first mealtime indicator is set from the first estimated mealtime to a second estimated mealtime based on a detection that a meal has been eaten or is likely to be eaten by the user at a time outside of the first estimated mealtime.

17. The device of claim 16, wherein the at least one processor is further configured to update the estimated mealtime from the first estimated mealtime to the second estimated mealtime in response to the mealtime score being above a predefined threshold at the time outside of the first estimated mealtime.

18. The device of claim 16, wherein the at least one processor is further configured to update the estimated mealtime from the first estimated mealtime to the second estimated mealtime in response to a number of mealtimes that are tracked over a period of time being detected as being outside of the first estimated mealtime.

19. The device of claim 15, wherein the device comprises a transceiver, and wherein the at least one processor is further configured to:
    transmit, via the transceiver, a message configured to control a basal rate of an insulin pump after detection of the mealtime based on the mealtime score.

20. The device of claim 15, wherein the at least one processor is further configured to use a weight value of the photograph indicator to determine the mealtime score, and wherein the weight value is different based on a confidence level that the photograph includes the meal-related item.

21. The device of claim 20, wherein the at least one processor is further configured to enable image processing of the photograph using a photo service, wherein the photo service includes a neural network image classifier capable of identifying various types of meal-related items that have been learned from prestored images, and wherein the meal-related items are identified based on at least one of textures, patterns, spatial density, or shapes of items in the photograph.

22. The device of claim 15, wherein the at least one processor is further configured to determine the mealtime score based on the keyword indicator, and wherein a weight value of the keyword indicator that is used for determining the mealtime score is different based on the keyword or a number of keywords detected.

23. The device of claim 15, wherein the device comprises a gyroscope or an accelerometer, wherein the position indicator indicates the user is in a sitting position, and wherein the position indicator is based on information from the gyroscope or the accelerometer.

24. The device of claim 15, wherein the respective value of each of the second plurality of mealtime detection indicators comprises a respective weight value.

25. The device of claim 15, wherein the keyword comprises at least one of a meal-related word or a meal-related location mined from a title of the pre-scheduled event, and wherein a weight value of the keyword indicator that is used for determining the mealtime score is different based on the keyword or a number of keywords detected.

26. The device of claim 15, wherein the at least one processor is further configured to:
    detect, prior to determining the mealtime score, that a current time is at least a predefined period of time since a last mealtime associated with the user.

27. The device of claim 15, wherein the device comprises a glucose meter.

28. The device of claim 15, wherein the mealtime score comprises a first mealtime score, wherein the information comprises first information, wherein the respective value comprises a first respective vale, the at least one processor being further configured to:
    process second information associated with each of the plurality of second mealtime detection indicators in parallel to generate a second respective value for each of the plurality of second mealtime indicators associated with the user;
    determine a second mealtime score based on the second respective value of each of the plurality of second mealtime detection indicators associated with the user;
    determine that the second mealtime score is above the mealtime threshold based on the second respective value associated with each of the second mealtime detection indicators; and
    provide the at least one mealtime alert to the user via the display to assist in treatment of a diabetic condition in response to the second mealtime score being above the mealtime threshold.

29. A computer-readable medium having stored thereon instructions that, when executed by at least one processing circuit, are configured to cause the at least one processing circuit to:
    detect a first mealtime indicator as a triggering event for determining a mealtime score for a user, wherein the first mealtime indicator is set at an estimated mealtime associated with the user;
    after detecting the first mealtime indicator, process information associated with each of a plurality of second mealtime detection indicators in parallel to generate a respective value for each of the plurality of second mealtime detection indicators associated with the user, wherein the plurality of second mealtime detection indicators comprise:
        a blood glucose indicator that indicates a blood glucose level of the user, and
        at least one of:
            a photograph indicator that is based on a photograph of a meal-related item;
            a position indicator that indicates the user is in a position of the user;
            a location indicator that indicates a location associated with a user; or
            a keyword indicator that indicates a keyword of a pre-scheduled event;
    process information associated with each of the plurality of second mealtime detection indicators in parallel to generate a respective value for each of the plurality of second mealtime indicators associated with the user;
    determine the mealtime score based on the respective value of each of the plurality of second mealtime detection indicators associated with the user;
    determine that the mealtime score is below a mealtime threshold based on the respective value associated with each of the second mealtime detection indicators; and
    prevent at least one mealtime alert from being provided to the user via a display based on the mealtime score being below the mealtime threshold, wherein the instructions are further configured to cause the at least one circuit to prevent the at least one mealtime alert from being provided via the display to save a power of the battery based on the estimated mealtime associated with the user failing to indicate a mealtime.

30. The computer-readable medium of claim 29, wherein the mealtime score comprises a first mealtime score, wherein the information comprises first information, wherein the respective value comprises a first respective vale, and wherein the instructions are further configured to cause the at least one processing circuit to:
    process second information associated with each of the plurality of second mealtime detection indicators in parallel to generate a second respective value for each of the plurality of second mealtime indicators associated with the user;

determine a second mealtime score based on the second respective value of each of the plurality of second mealtime detection indicators associated with the user;

determine that the second mealtime score is above the mealtime threshold based on the second respective value associated with each of the second mealtime detection indicators; and provide the at least one mealtime alert to the user via the display to assist in treatment of a diabetic condition in response to the second mealtime score being above the mealtime threshold.

* * * * *